United States Patent
Kanner

(10) Patent No.: US 8,563,579 B2
(45) Date of Patent: Oct. 22, 2013

(54) α-7 NICOTINIC ACETYLCHOLINE RECEPTOR ALLOSTERIC MODULATORS, THEIR DERIVATIVES AND USES THEREOF

(75) Inventor: Richard Kanner, Santa Ana, CA (US)

(73) Assignee: Anvyl LLC, Irvine, CA (US)

( * ) Notice: Subject to any disclaimer, the term of this patent is extended or adjusted under 35 U.S.C. 154(b) by 569 days.

(21) Appl. No.: 12/688,650

(22) Filed: Jan. 15, 2010

(65) Prior Publication Data
US 2010/0190819 A1 Jul. 29, 2010

Related U.S. Application Data

(60) Provisional application No. 61/145,027, filed on Jan. 15, 2009.

(51) Int. Cl.
*A61K 31/04* (2006.01)
*C07D 215/38* (2006.01)

(52) U.S. Cl.
USPC .......................... 514/312; 546/159

(58) Field of Classification Search
USPC .......................... 546/159; 514/312
See application file for complete search history.

(56) References Cited

U.S. PATENT DOCUMENTS

| 5,294,620 A | * | 3/1994 | Ratcliffe et al. ............ 514/300 |
| 2005/0065178 A1 | | 3/2005 | Basha et al. |

FOREIGN PATENT DOCUMENTS

| EP | 516392 | * 12/1992 |
| WO | 2006071184 | 6/2006 |

OTHER PUBLICATIONS

Becalli, E., "Oxidation of 4-Aryl-Substituted Isoxazolin-5-ones. A New Synthesis of 2,5-Diaryl-1,3-oxazin-6-ones" J. Org. Chem. vol. 49, 1984, p. 4287-4290.

Burgart, Y. et al., "A route to ethyl α-pentafluorobenzoyl-β-oxobutanoate via its copper (II) chelate" Mendeleev Communications, 2001, p. 76.
Croisy-Delcet, M. et al., "Synthesis of 11-Aminosubstituted 6, 8-Dimethyl-12H-[1]-Benzo[5,6] Thiopyrano-[2,3-c]Quinolin-12-Ones as Benzo Analogues of Lucanthone" Heterocycles, vol. 32, No. 10, 1991, p. 1933-1945.
Dai, Y. et al., Identification of aminopyrazolopyridine ureas as potent VEGFR/PDGFR multitargeted kinase inhibitors, Bioorganic & Medicinal Chemistry Letters, vol. 18, 2008, p. 386-390.
Giannouli, V. et al., "Design, Synthesis, and Evaluation of the Antiproliferative Activity of a Series of Novel Fused Xanthenone Aminoderivatives in Human Breast Cancer Cells" J. Med. Chem., 2007 vol. 50, p. 1716-1719.
Perner, "5,6,7-Trisubstituted 4-Aminopyrido[2,3-d]pyrimidines as Novel Inhibitors of Adenosine Kinase" J. Med. Chem., vol. 46, 2003, p. 5249-5256.
International Search Report and Written Opinion mailed Mar. 18, 2010 in corresponding PCT application PCT/US2010/021248.
Wentland, M. et al., "Mammalian Topoisomerase II Inhibitory Activity of 1-Cyclopropyl-6,8-difluoro-1,4-dihydro-7-(2,6-dimethyl-4-pyridinyl)-4-oxo-3-quinolinecarboxylic Acid and Related Derivatives" J. Med. Chem., vol. 36, 1993, p. 2801-2809.

* cited by examiner

*Primary Examiner* — D M Seaman
(74) *Attorney, Agent, or Firm* — Wolff IP, A Prof. Corp.; Jessica R. Wolff

(57) ABSTRACT

The present application is related to compounds represented by Formula I, which are novel allosteric modulators of α7nAChR. The application also discloses the treatment of disorders that are responsive to modulation of acetylcholine action on α7nAChR in a mammal by administering an effective amount of a compound of Formula I.

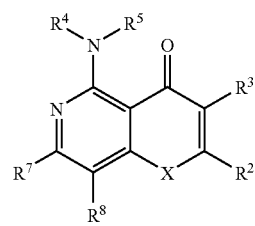

20 Claims, No Drawings

α-7 NICOTINIC ACETYLCHOLINE RECEPTOR ALLOSTERIC MODULATORS, THEIR DERIVATIVES AND USES THEREOF

RELATED APPLICATIONS

This application claims the benefit of U.S. Provisional Application Ser. No. 61/145,027, filed Jan. 15, 2009, which is hereby incorporated by reference in its entirety.

BACKGROUND

The disclosure of the present application is in the field of medicinal chemistry. In particular, this application discloses a class of novel compounds that allosterically modulate α7 nicotinic acetylcholine receptor (α7nAChR) and may be used to treat disorders amenable to modulation of the α7nAChR.

α7nAChRs belong to the ligand-gated ion channel superfamily of Cys-loop receptors. The Cys-loop superfamily includes muscle and neuronal nAChRs, 5-hydroxytryptamine type 3 ($5HT_3$), γ-aminobutyric acid$_A$ ($GABA_A$), $GABA_C$ and glycine receptors. α7nAChRs are ion channels that recognize acetylcholine and choline as the endogenous orthosteric ligand and also bind nicotine at the orthosteric site. α7 nAChRs contain 5 orthosteric receptor sites per receptor. Agonist binding to the orthosteric site effects functional states of the receptor depending on the concentration and kinetics of agonist application. Four functional states have been described for α7 nAChRs: one open and three closed states (resting, fast-onset desensitized, slow-onset desensitized). Unlike agonists, allosteric modulators of α7nAChRs do not bind to the orthosteric site, and cannot affect the functional state of the ion channel by themselves. An allosteric modulator of α7nAChRs requires the presence of an agonist to open the channel. Positive allosteric modulators lower the energy barrier between resting and active states of the protein and increase the agonist-evoked response; negative allosteric modulators increase this energy barrier and cause a reduction in the agonist response. In the brain, activation of neuronal α7nAChRs mediates fast synaptic transmission and controls synaptic transmission by the major inhibitory and excitatory neurotransmitters, GABA and glutamate.

α7nAChRs mediate the predominant nicotinic current in hippocampal neurons. α7nAChR was initially identified from a chick brain library as an α-bungarotoxin binding protein that exhibits ~40% sequence homology to other nAChRs. α7nAChRs share similar features of other neuronal and muscle nAChRs such as a pentameric Cys-loop receptor structure and M2 segment of each subunit lining of the channel pore, however α7nAChRs exhibits a homopentameric structure when reconstituted in *Xenopus* oocytes, a characteristic shared only with α8 and α9 nAChRs. Heterologously expressed homomeric α7nAChRs in *Xenopus* oocytes are inactivated by α-bungarotoxin with high affinity, whereas other nAChRs are not. α7nAChRs have also been pharmacologically identified by distinct types of whole cell currents elicited by nicotinic agonists in hippocampal neurons. When exposed to various nicotinic agonists, whole cell recordings from cultured hippocampal neurons show, in general, type IA currents that have a very brief open time, high conductance, very high $Ca^{++}$ permeability, decay rapidly, and are sensitive to blockade by methyllycaconitine (MLA) and α-bungarotoxin. The properties of these nicotinic currents in hippocampal neurons correspond to the currents mediated by α7nAChRs expressed in oocytes.

SUMMARY OF THE INVENTION

Briefly, this invention is generally directed to allosteric modulators of α7nAChR, as well as to methods for their preparation and use, and to pharmaceutical compositions containing the same. More specifically, the allosteric α7nAChR modulators of this invention are compounds represented by the general structure:

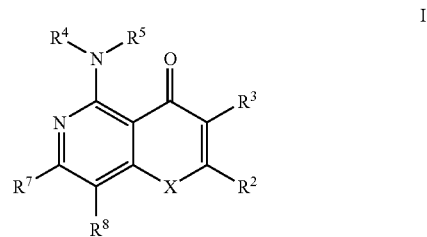

I including pharmaceutically acceptable salts, esters, solvates, and prodrugs thereof, wherein $R^2$, $R^3$, $R^4$, $R^5$, $R^7$, $R^8$, and X are as defined below.

Further, the present invention is directed to $^3H$, $^{11}C$, $^{18}F$, $^{35}S$, $^{36}Cl$, $^{14}C$ and $^{125}I$ radiolabeled compounds of Formula I and their use as radioligands for their binding site on the α7nAChR complex.

This invention also is directed to methods of treating disorders responsive to enhancement of acetylcholine action on α7nAChRs in a mammal by administering an effective amount of a compound of Formula I as described herein. Compounds of the present invention may be used to treat a variety of disorders, including of the central nervous system (CNS). Disorders of the CNS include but are not limited to neurodegenerative diseases, senile dementias, schizophrenia, Alzheimer's disease, learning deficit, cognition deficit, memory loss, Lewy Body dementia, attention-deficit disorder, attention deficit hyperactivity disorder, anxiety, mania, manic depression, Parkinson's disease, Huntington's disease, amyotrophic lateral sclerosis, brain inflammation and Tourette's syndrome. In addition, compounds of the present invention may be used to treat pain, inflammation, septic shock, ulcerative colitis and irritable bowel syndrome.

The present invention also is directed to pharmaceutical formulations which include a compound of the present invention. Such formulations contain a therapeutically effective amount of a compound of Formula I and one or more pharmaceutically acceptable carriers or diluents.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION

In one aspect, the present invention is directed to a compound of Formula I:

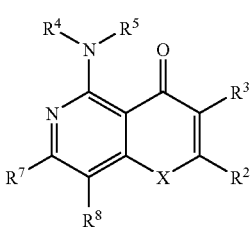

I or a pharmaceutically acceptable salt, ester, prodrug or solvate thereof, wherein:

X is O, S or N—$R^1$;

$R^1$ is hydrogen, $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^1$ is aryl, heteroaryl, cycloalkyl, cycloalkenyl, heterocycloalkyl or heterocycloalkenyl, wherein said heterocycloalkyl is optionally fused with phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^2$ is hydrogen, halogen, nitrile, nitro or C(═O)$R^9$; or $R^2$ is $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^2$ is aryl, carbon-attached heteroaryl, cycloalkyl, cycloalkenyl, carbon-attached heterocycloalkyl or carbon-attached heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^3$ is aryl, heteroaryl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^4$ is hydrogen, $C_{1-6}$ alkyl, $C_{2-6}$ alkenyl, $C_{2-6}$ alkynyl, or $C_{1-8}$ haloalkyl, wherein each of said alkyl, alkenyl, alkynyl, and haloalkyl is optionally substituted with one or more $R^9$; or $R^4$ is aryl, heteroaryl, cycloalkyl, cycloalkenyl, heterocycloalkyl or heterocycloalkenyl, wherein heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^5$ is hydrogen, $C_{1-6}$ alkyl, $C_{2-6}$ alkenyl, $C_{2-6}$ alkynyl, $C_{1-6}$ haloalkyl, —C(═O)$R^9$, —S(═O)$_{0-2}R^9$, —S(═O)$_{0-2}$-A-$R^9$ or -A-C(═O)$R^9$, wherein each of said alkyl, alkenyl, alkynyl, and haloalkyl is optionally substituted with one or more $R^9$; or $R^5$ is aryl, heteroaryl, cycloalkyl, cycloalkenyl, heterocycloalkyl or heterocycloalkenyl, wherein said heterocycloalkyl is optionally fused with a phenyl or a 5-6 membered heteroaryl, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$; or $R^4$ and $R^5$ taken together with the nitrogen to which they are attached form a heteroaryl, a heterocycloalkyl or a heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said heteroaryl, heterocycloalkyl, and heterocycloalkenyl is optionally substituted with 1-5 $R^{10}$;

each of $R^7$ and $R^8$ is independently hydrogen, $C_{1-8}$ alkyl, $C_{1-8}$ alkoxy, $C_{2-8}$ alkenyl, $C_{2-8}$ alkynyl, $C_{1-8}$ haloalkyl, or $C_{1-8}$ haloalkoxy; wherein each of said alkyl, alkenyl, alkynyl, haloalkyl, and haloalkoxy is optionally substituted with one or more $R^9$; or each of $R^7$ and $R^8$ is independently halogen, nitrile, nitro, hydroxyl, —C(═O)$R^9$, —S(═O)$_{0-2}R^9$, —NR$^4$R$^5$, —S(═O)$_{0-2}$-A-$R^9$ or -A-C(═O)$R^9$; or each of $R^7$ and $R^8$ is independently aryl, heteroaryl, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$; or $R^9$ is hydroxyl, $C_{1-6}$ alkoxy, $C_{1-8}$ haloalkoxy, $C_{3-6}$ cycloalkoxy or NR$^{11}$R$^{12}$; or $R^9$ is aryl, heteroaryl, cycloalkyl, or cycloalkenyl, wherein each of said aryl, heteroaryl, cycloalkyl and cycloalkenyl are optionally substituted with 1-5 $R^{10}$; or $R^9$ is heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said heterocycloalkyl and said heterocycloalkenyl is optionally substituted with 1-5 $R^{10}$;

$R^{10}$ is nitro, nitrile, hydroxyl, halogen, $C_{1-6}$ acyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cycloalkoxy, cycloalkyloxy, aryl, heteroaryl, —NR$^{11}$R$^{12}$, —C(═O)OR$^{11}$, —C(═O)NHR$^{11}$, —NHC(═O)R$^{13}$, —NHS(═O)$_2$R$^{13}$, —S(═O)$_{0-2}$R$^{13}$, —S(═O)$_2$NHR$^{11}$, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O); wherein each of said alkyl, alkenyl, alkynyl, haloalkyl, alkoxy, haloalkoxy, cycloalkoxy, cycloalkyloxy, aryl, heteroaryl, cycloalkyl, cycloalkenyl, heterocycloalkyl, and heterocycloalkenyl is optionally substituted;

each of R$^{11}$ and R$^{12}$ is independently hydrogen, $C_{1-6}$ alkyl, $C_{2-6}$ alkenyl, $C_{2-6}$ alkynyl, $C_{1-6}$ haloalkyl, cycloalkyl or cycloalkenyl; wherein each of said alkyl, alkenyl, alkynyl, haloalkyl, cycloalkyl and cycloalkenyl is optionally substituted with one or more $R^9$;

$R^{13}$ is $C_{1-6}$ alkyl, $C_{2-6}$ alkenyl, $C_{2-6}$ alkynyl, $C_{1-6}$ haloalkyl, $C_{3-6}$ cycloalkyl or $C_{4-6}$ cycloalkenyl; wherein each of said alkyl, alkenyl, alkynyl, haloalkyl, cycloalkyl and cycloalkenyl is optionally substituted; and A is $C_{1-4}$ alkyl, $C_{2-8}$ alkenyl or $C_{1-8}$ haloalkyl.

In one embodiment X is NR$^1$. In another embodiment X is O. In another embodiment X is S.

In one embodiment, $R^1$ is hydrogen, $C_{1-6}$ alkyl, $C_{1-6}$ haloalkyl or $C_{1-6}$ cycloalkyl, wherein each of said $C_{1-6}$ alkyl and $C_{1-6}$ haloalkyl is optionally substituted with one or more $R^9$ and said $C_{1-6}$ cycloalkyl is optionally substituted with 1-5 $R^{10}$. In one such embodiment, $R^1$ is hydrogen or $C_{1-6}$ alkyl. In one embodiment, $R^1$ is hydrogen. In another embodiment, $R^1$ is methyl, ethyl or cyclopropyl.

In one embodiment, $R^2$ is hydrogen, $C_{1-6}$ alkyl, $C_{1-6}$ haloalkyl or $C_{1-6}$ cycloalkyl, wherein each of said $C_{1-6}$ alkyl and $C_{1-6}$ haloalkyl is optionally substituted with one or more $R^9$ and said $C_{1-6}$ cycloalkyl is optionally substituted with 1-5 $R^{10}$. In one such embodiment, $R^2$ is hydrogen or $C_{1-6}$ alkyl. In one embodiment, $R^2$ is hydrogen. In another embodiment, $R^2$ is methyl or ethyl.

In one embodiment, $R^3$ is aryl or heteroaryl, wherein each of said aryl and heteroaryl is optionally substituted with 1-5 $R^{10}$. In one such embodiment, $R^3$ is aryl substituted with halogen, $C_{1-6}$ alkyl or $C_{1-6}$ alkoxy.

In one embodiment $R^4$ is hydrogen.

In one embodiment $R^5$ is $C_{1-6}$ alkyl optionally substituted with one or more $R^9$. In one such embodiment $R^9$ is aryl or cycloalkyl. In one such embodiment $R^9$ is aryl.

In one embodiment each of $R^7$ and $R^8$ is independently hydrogen, $C_{1-6}$ alkyl, $C_{1-6}$ haloalkyl or $C_{1-6}$ cycloalkyl. In one embodiment, each of $R^7$ and $R^8$ is independently hydrogen.

In one embodiment, $R^9$ is aryl, heteroaryl or cycloalkyl. In one such embodiment, $R^9$ is aryl. In another such embodiment, $R^9$ is heteroaryl. In another such embodiment, $R^9$ is cycloalkyl.

In one embodiment, $R^{10}$ is halogen, $C_{1-6}$ alkyl, $C_{1-6}$ haloalkyl, $C_{1-6}$ alkoxy or cycloalkyloxy. In one such embodiment, $R^{10}$ is halogen or $C_{1-6}$ alkyl. In one embodiment, $R^{10}$ is halogen. In another embodiment, $R^{10}$ is $C_{1-6}$ alkyl.

DEFINITIONS

Unless specifically noted otherwise herein, the definitions of the terms used are standard definitions used in the art of organic synthesis and pharmaceutical sciences.

The term "halogen" as used herein refers to a halogen radical selected from fluoro, chloro, bromo and iodo.

The term "nitrile" refers to —C≡N.

The term "nitro" refers to —NO$_2$.

The term "alkyl" refers to a saturated aliphatic hydrocarbon radical. "Alkyl" refers to both branched and unbranched alkyl groups. Examples of "alkyl" include alkyl groups that are straight chain alkyl groups containing from one to ten carbon atoms and branched alkyl groups containing from three to ten carbon atoms. "Alkyl" includes but is not limited to straight chain alkyl groups containing from one to six carbon atoms and branched alkyl groups containing from three to six carbon atoms. This term is exemplified by groups such as methyl, ethyl, n-propyl, 1-methylethyl (isopropyl), 1,1-dimethylethyl (tert-butyl), and the like. It may be abbreviated "Alk". It should be understood that any combination term using an "alk" or "alkyl" prefix refers to analogs according to the above definition of "alkyl". For example, terms such as "alkoxy", "alkylthio", "alkylamino" refer to alkyl groups linked to a second group via an oxygen, sulfur, or nitrogen atom, respectively.

The term "haloalkyl" refers to an alkyl group in which one or more hydrogen atoms are replaced with halogen atoms. This term includes but is not limited to groups such as trifluomethyl. In one embodiment the haloalkyl groups are alkyl groups substituted with one or more fluoro or chloro. The term "haloalkoxy" refers to haloalkyl groups linked to a second group via an oxygen atom.

The term "alkenyl" refers to a mono or polyunsaturated aliphatic hydrocarbon radical. The mono or polyunsaturated aliphatic hydrocarbon radical contains at least one carbon-carbon double bond. "Alkenyl" refers to both branched and unbranched alkenyl groups, each optionally partially or fully halogenated. Examples of "alkenyl" include alkenyl groups that are straight chain alkenyl groups containing from two to ten carbon atoms and branched alkenyl groups containing from three to ten carbon atoms. Other examples include alkenyl groups which are straight chain alkenyl groups containing from two to six carbon atoms and branched alkenyl groups containing from three to six carbon atoms. Alkenyl groups include but are not limited to ethenyl, propenyl, n-butenyl, isobutenyl, 3-methylbut-2-enyl, n-pentenyl, heptenyl, octenyl, decenyl, and the like.

The term "alkynyl" refers to a mono or polyunsaturated aliphatic hydrocarbon radical. The mono or polyunsaturated aliphatic hydrocarbon radical contains at least one carbon-carbon triple bond. "Alkynyl" refers to both branched and unbranched alkynyl groups, each optionally partially or fully halogenated. Examples of "alkynyl" include alkynyl groups that are straight chain alkynyl groups containing from two to ten carbon atoms and branched alkynyl groups containing from four to ten carbon atoms. Other examples include alkynyl groups that are straight chain alkynyl groups containing from two to six carbon atoms and branched alkynyl groups containing from four to six carbon atoms. This term is exemplified by groups such as ethynyl, propynyl, octynyl, and the like.

The term "cycloalkyl" refers to the mono- or polycyclic analogs of an alkyl group, as defined above. Unless otherwise specified, the cycloalkyl ring may be attached at any carbon atom that results in a stable structure and, if substituted, may be substituted at any suitable carbon atom which results in a stable structure. Examples of cycloalkyl groups are saturated cycloalkyl groups containing from three to ten carbon atoms. Other examples include cycloalkyl groups containing three to eight carbon atoms or three to six carbon atoms. Exemplary cycloalkyl groups include but are not limited to cyclopropyl, cyclobutyl, cyclopentyl, cyclohexyl, cyclooctyl, cyclononyl, cyclodecyl, norbornane, adamantyl, and the like.

The term "cycloalkenyl" refers to the mono- or polycyclic analogs of an alkenyl group, as defined above. Unless otherwise specified, the cycloalkenyl ring may be attached at any carbon atom that results in a stable structure and, if substituted, may be substituted at any suitable carbon atom which results in a stable structure. Examples of cycloalkenyl groups are cycloalkenyl groups containing from four to ten carbon atoms. Other examples include cycloalkenyl groups containing four to eight carbon atoms or four to six carbon atoms. Exemplary cycloalkenyl groups include but are not limited to cyclobutenyl, cyclopentenyl, cyclohexenyl, norbornene, and the like.

The term "heterocycloalkyl" refers to the mono- or polycyclic structures of "cycloalkyl" where one or more of the carbon atoms are replaced by one or more atoms independently selected from nitrogen, oxygen, or sulfur atoms. Any nitrogen atom maybe optionally oxidized or quaternized, and any sulfur atom maybe optionally oxidized. Generally, the heteroatoms may be selected from the group consisting of N, S, S═O, S(═O)$_2$, and O. Unless otherwise specified, the heterocycloalkyl ring may be attached at any carbon atom or heteroatom that results in a stable structure and, if substituted, may be substituted at any suitable carbon atom or heteroatom which results in a stable structure. Examples of heterocycloalkyl groups are saturated heterocycloalkyl groups containing from two to nine carbon atoms and one to four heteroatoms. Generally, 5-7 membered heterocycloalkyl groups contain 3-6 carbon atoms and 1-2 heteroatoms independently selected from the group consisting of N, S, S=O, S(=O)$_2$, and O. Examples of heterocycloalkyl groups include but are not limited to morpholino, pyrazino, tetrahydrofurano, and the like. "Carbon-attached heterocycloalkyl" refers to a heterocycloalkyl group which is bound via a constituent carbon atom. A heterocycloalkyl that is fused with a phenyl can include, but is not limited to, the following:

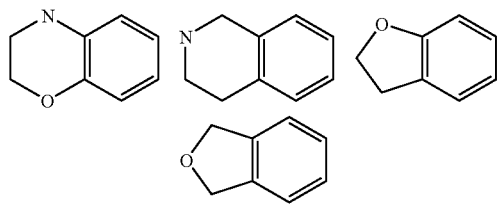

A heterocycloalkyl that is fused with a 5-6 membered heteroaryl can include, but is not limited to, the following:

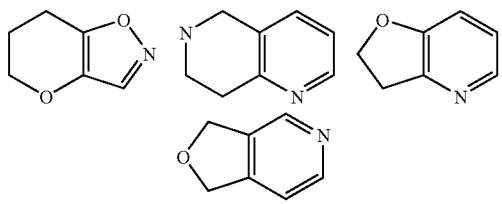

The term "heterocycloalkenyl" refers to the mono- or polycyclic structures of "cycloalkenyl" where one or more of the carbon atoms are replaced by one or more atoms independently chosen from nitrogen, oxygen, or sulfur atoms. Any nitrogen atom maybe optionally oxidized or quaternized, and any sulfur atom maybe optionally oxidized. Unless otherwise specified, the heterocycloalkenyl ring may be attached at any carbon atom or heteroatom that results in a stable structure and, if substituted, may be substituted at any suitable carbon atom or heteroatom which results in a stable structure. Examples of heterocycloalkenyl groups are saturated heterocycloalkenyl groups containing from two to nine carbon atoms and one to four heteroatoms. Generally, 5-7 membered heterocycloalkenyl groups contain 3-6 carbon atoms and 1-2 heteroatoms independently selected from the group consisting of N, S, S=O, S(=O)$_2$, and O. Examples of heterocycloalkenyl groups include but are not limited to dihydropyran, dihydrofuran, and the like. "Carbon-attached heterocycloalkenyl" refers to a heterocycloalkenyl group which is bound via a constituent carbon atom.

The term "cycloalkyloxy" refers to a monovalent radical of the formula —O-cycloalkyl, i.e., a cycloalkyl group linked to a second group via an oxygen atom, wherein the cycloalkyl group is as defined above including optionally substituted cycloalkyl groups as also defined herein.

The term "acyl" refers to a monovalent radical of the formula —C(=O)-alkyl and —C(=O)-cycloalkyl, i.e., an alkyl or cycloalkyl group linked to a second group via carbonyl group C(=O), wherein said alkyl maybe further substituted with cycloalkyl, aryl, or heteroaryl. Examples of acyl groups include —C(=O)Me (acetyl), —C(=O)CH$_2$-cyclopropyl (cyclopropylacetyl), —C(=O)CH$_2$Ph (phenylacetyl), and the like.

The term "aryl" refers to 6-10 membered mono- or polycyclic aromatic carbocycles, for example, phenyl and naphthyl. Unless otherwise specified, the aryl ring may be attached at any carbon atom that results in a stable structure and, if substituted, may be substituted at any suitable carbon atom which results in a stable structure. The term "aryl" refers to non-substituted aryls and aryls optionally substituted with one or more substituents. Aryl maybe abbreviated "Ar". It should be understood that any combination term using an "ar" or "aryl" prefix refers to analogs according to the above definition of "aryl". For example, terms such as "aryloxy", "arylthio", and "arylamino" refer to aryl groups linked to a second group via an oxygen, sulfur, or nitrogen atom, respectively.

The term "heteroaryl" refers to a stable 5-8 membered monocyclic or 8-11 membered bicyclic aromatic heterocycle radical. In one embodiment the monocyclic groups are 5 or 6 membered. Each heteroaryl contains 1-10 carbon atoms and from 1 to 5 heteroatoms independently chosen from nitrogen, oxygen and sulfur, wherein any sulfur heteroatom may optionally be oxidized and any nitrogen heteroatom may optionally be oxidized or quaternized. Unless otherwise specified, the heteroaryl ring may be attached at any suitable heteroatom or carbon atom that results in a stable structure and, if substituted, may be substituted at any suitable heteroatom or carbon atom which results in a stable structure. The term "heteroaryl" includes heteroaryl groups that are non-substituted or those optionally substituted. Generally, heteroaryl groups containing 2-9 carbon atoms and 1-4 heteroatoms independently selected from the group N, S, S=O, S(=O)$_2$, and O. Examples of "heteroaryl" include but are not limited to radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzothiazolyl, benzoxazolyl, benzisoxazolyl, benzisothiazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl. Terms such as "heteroaryloxy", "heteroarylthio", "heteroarylamino" refer to heteroaryl groups linked to a second group via an oxygen, sulfur, or nitrogen atom, respectively.

Each of the groups described herein, including alkyl, haloalkyl, alkenyl, alkynyl, cycloalkyl, cycloalkenyl, heterocycloalkyl, heterocycloalkenyl, cycloalkyloxy, acyl, aryl, heteroaryl, all are optionally substituted.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution. Exemplary optional substituents include one or more of the following groups: halogen, C$_1$-C$_6$ alkyl, C$_3$-C$_6$ cycloalkyl, C$_1$-C$_6$ haloalkyl C$_2$-C$_6$ alkenyl, C$_4$-C$_6$ cycloalkenyl, C$_2$-C$_6$ alkynyl, nitro, nitrile, cyano, hydroxyl, C$_1$-C$_6$ alkoxy, C$_1$-C$_6$ haloalkoxy, C$_3$-C$_6$ cycloalkoxy, amino, C$_1$-C$_6$ alkylamino (for example, —NHMe- or —N(Me)$_2$), C$_1$-C$_6$ acyl, thiol, alkylthio, and carboxylic acid. Additional optional substituents include aryl, heteroaryl, heterocycloalkyl and heterocycloalkenyl. Such substituents can further be substituted with optionally selected groups to foam a stable structure.

As used herein "solvate" refers to a complex of variable stoichiometry formed by a solute (e.g. a compound of formula (I) or a salt, ester or prodrug thereof) and a solvent. Such solvents for the purpose of the invention may not interfere with the biological activity of the solute. Examples of suitable solvents include water, methanol, ethanol and acetic acid. Generally the solvent used is a pharmaceutically acceptable solvent. Examples of suitable pharmaceutically acceptable solvents include water, ethanol and acetic acid. Generally the solvent used is water.

"Isomers" mean any compound with an identical molecular formula but having a difference in the nature or sequence of bonding or arrangement of the atoms in space. Examples of such isomers include, for example, E and Z isomers of double bonds, enantiomers, and diastereomers. Compounds of the present invention depicting a bond with a straight line or "squiggly line" representation that is attached to a double bond, unless specifically noted otherwise, is intended to encompass a single isomer and/or both isomers of the double bond as shown below mean any compound with an identical molecular formula but having a difference in the nature or sequence of bonding or arrangement of the atoms in space.

As used herein "allosteric modulator" of α7nAChR refers to a compound that that binds allosterically to α7nAChR, thereby increasing (positive allosteric modulator) or decreasing (negative allosteric modulator) the agonist-evoked response.

As used herein a "disorder amenable to modulation of α7nAChR" refers to a disorder associated with α7nAChR dysfunction and/or a disorder in which α7nACh receptors are involved. Such disorders include, but are not limited to neurodegenerative diseases, senile dementias, schizophrenia, Alzheimer's disease, learning deficits, cognition deficits memory loss, Lewy Body dementia, attention-deficit disorder, attention deficit hyperactivity disorder, anxiety, mania, manic depression, Parkinson's disease, Huntington's disease, amyotrophic lateral sclerosis, brain inflammation, Tourette's syndrome, pain, inflammation, septic shock, ulcerative colitis and irritable bowel syndrome.

As used herein "a cognitive disorder related to learning or memory" refers to a mental disorder that affects cognitive functions, such as memory, learning, perception, problem-solving, conceptualization, language, reading comprehension, linguistic comprehension, verbal comprehension, math comprehension, visual comprehension and attention. Cognitive disorders related to learning or memory include, but are not limited to, mild cognitive impairment, age related cognitive decline, senile dementia and Alzheimer's disease.

Formulations

Compounds of the invention may be administered orally in a total daily dose of about 0.01 mg/kg/dose to about 100 mg/kg/dose, typically from about 0.1 mg/kg/dose to about 10 mg/kg/dose. The use of time-release preparations to control the rate of release of the active ingredient may be employed. The dose may be administered in as many divided doses as is convenient. When other methods are used (e.g. intravenous administration), compounds may be administered at a rate from 0.05 to 10 mg/kg/hour, typically from 0.1 to 1 mg/kg/hour. Such rates are easily maintained when these compounds are intravenously administered as discussed below.

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally employed.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax maybe employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above.

Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions. The pharmaceutical composition can be prepared to provide easily measurable amounts for administration. For example, an aqueous solution intended for intravenous infusion should contain from about 3 to 330 μg of the active ingredient per milliliter of solution in order that infusion of a suitable volume at a rate of about 30 mL/hr can occur.

As noted above, formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach. This is particularly advantageous with the compounds of formula I when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Suitable unit dosage formulations are those containing a daily dose or unit, daily sub-dose, or an appropriate fraction thereof, of a compound of Formula I.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

In one variation of the compounds of Formula I, X is NR$^1$ such that representative allosteric α7nAChR modulators of this invention include compounds having the structure of Formula II:

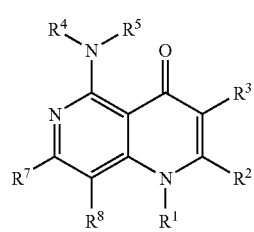

In another variation of the compounds of Formula I, X is NR¹ and R³ is

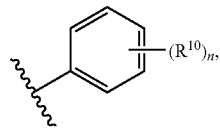

such that representative allosteric α7nAChR modulators of this invention include compounds having the structure of Formula IIA:

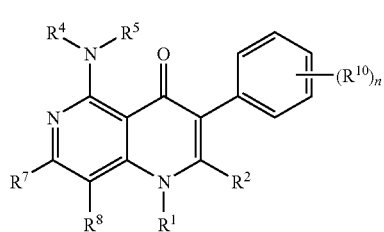

IIA

In yet another variation of the compounds of Formula I, X is O, such that representative allosteric α7nAChR modulators of this invention include compounds having the structure of Formula III:

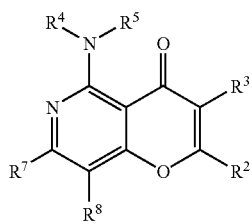

III

In still another variation of the compounds of Formula I, X is S, such that representative allosteric α7nAChR modulators of this invention include compounds having the structure of Formula IV:

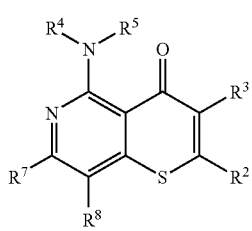

IV

In one aspect, compounds of Formula I include:
3-(4-Chlorophenyl)-1,4-dihydro-4-oxo-5-(2-pyridylmethylamino)-1,6-naphthyridine (Compound 1),
3-(4-Chlorophenyl)-1,4-dihydro-4-oxo-5-(4-pyridylmethylamino)-1,6-naphthyridine (Compound 2),
3-(4-Chlorophenyl)-1,4-dihydro-4-oxo-5-phenylamino-1,6-naphthyridine (Compound 3),
3-(4-Chlorophenyl)-1,4-dihydro-4-oxo-5-propylamino-1,6-naphthyridine (Compound 4),
3-(4-Chlorophenyl)-1,4-dihydro-4-oxo-5-benzylamino-1,6-naphthyridine (Compound 5),
3-(4-Chlorophenyl)-1,4-dihydro-4-oxo-5-cyclopropylamino-1,6-naphthyridine (Compound 6),
3-(4-Chlorophenyl)-1,4-dihydro-4-oxo-5-cyclopentylamino-1,6-naphthyridine (Compound 7),
3-(4-Chlorophenyl)-1,4-dihydro-4-oxo-5-cyclopropylmethylamino-1,6-naphthyridine (Compound 8),
3-(4-Chlorophenyl)-1,4-dihydro-4-oxo-5-ethylamino-1,6-naphthyridine (Compound 9),
3-(4-Chlorophenyl)-1,4-dihydro-4-oxo-5-(4-fluorophenylamino)-1,6-naphthyridine (Compound 10),
3-(4-Chlorophenyl)-1,4-dihydro-4-oxo-5-(4-chlorophenylamino)-1,6-naphthyridine (Compound 11),
3-(4-Chlorophenyl)-1,4-dihydro-4-oxo-5-tert-butylamino-1,6-naphthyridine (Compound 12),
3-(4-Chlorophenyl)-1,4-dihydro-4-oxo-5-cyclohexylmethylamino-1,6-naphthyridine (Compound 13),
3-(4-Chlorophenyl)-1,4-dihydro-4-oxo-5-methylamino-1,6-naphthyridine (Compound 14),
3-(4-Methoxyphenyl)-1,4-dihydro-4-oxo-5-phenylamino-1,6-naphthyridine (Compound 15),
3-(4-Ethoxyphenyl)-1,4-dihydro-4-oxo-5-phenethylamino-1,6-naphthyridine (Compound 16),
3-(4-Ethoxyphenyl)-1,4-dihydro-4-oxo-5-phenylamino-1,6-naphthyridine (Compound 17),
3-(4-Ethoxyphenyl)-1,4-dihydro-4-oxo-5-benzylamino-1,6-naphthyridine (Compound 18),
3-(4-Ethoxyphenyl)-1,4-dihydro-4-oxo-5-cyclohexylmethylamino-1,6-naphthyridine (Compound 19),
3-(4-Ethoxyphenyl)-1,4-dihydro-4-oxo-5-ethylamino-1,6-naphthyridine (Compound 20),
3-(4-Ethoxyphenyl)-1,4-dihydro-4-oxo-5-cyclopropylamino-1,6-naphthyridine (Compound 21),
3-(4-Ethoxyphenyl)-1,4-dihydro-4-oxo-5-cyclopropylmethylamino-1,6-naphthyridine (Compound 22),
3-(4-Ethoxyphenyl)-1,4-dihydro-4-oxo-5-cyclobutylamino-1,6-naphthyridine (Compound 23),
3-(4-Ethoxyphenyl)-1,4-dihydro-4-oxo-5-propylamino-1,6-naphthyridine (Compound 24),
3-(4-Ethoxyphenyl)-1,4-dihydro-4-oxo-5-cyclopentylamino-1,6-naphthyridine (Compound 25),
3-(4-Ethoxyphenyl)-1,4-dihydro-4-oxo-5-amino-1,6-naphthyridine (Compound 26),
3-(p-Tolyl)-1,4-dihydro-4-oxo-5-phenethylamino-1,6-naphthyridine (Compound 27),
3-(4-Chlorophenyl)-1,4-dihydro-1-benzyl-4-oxo-5-benzylamino-1,6-naphthyridine (Compound 28),
3-(4-Chlorophenyl)-1,4-dihydro-1-cyclopropylmethyl-4-oxo-5-benzylamino-1,6-naphthyridine (Compound 29),
3-(4-Chlorophenyl)-1,4-dihydro-1-butyl-4-oxo-5-benzylamino-1,6-naphthyridine (Compound 30),
3-(4-Ethoxyphenyl)-1,4-dihydro-1-methyl-4-oxo-5-phenethylamino-1,6-naphthyridine (Compound 31),
3-(4-Ethoxyphenyl)-1,4-dihydro-1-methyl-4-oxo-5-benzylamino-1,6-naphthyridine (Compound 32),
3-(4-Ethoxyphenyl)-1,4-dihydro-1-methyl-4-oxo-5-cyclohexylmethylamino-1,6-naphthyridine (Compound 33),
3-(4-Ethoxyphenyl)-1,4-dihydro-1-ethyl-4-oxo-5-phenethylamino-1,6-naphthyridine (Compound 34),
3-(4-Ethoxyphenyl)-1,4-dihydro-1-methyl-4-oxo-5-propylamino-1,6-naphthyridine (Compound 35),
3-(4-Ethoxyphenyl)-1,4-dihydro-1-methyl-4-oxo-5-cyclobutylamino-1,6-naphthyridine (Compound 36),
3-(4-Ethoxyphenyl)-1,4-dihydro-1-methyl-4-oxo-5-ethylamino-1,6-naphthyridine (Compound 37), 3-(4-Ethoxyphenyl)-1,4-dihydro-1-methyl-4-oxo-5-cyclopropylamino-1,6-naphthyridine (Compound 38),
3-(4-Ethoxyphenyl)-1,4-dihydro-1-methyl-4-oxo-5-cyclopropylmethylamino-1,6-naphthyridine (Compound 39),
3-(4-Ethoxyphenyl)-1,4-dihydro-1-methyl-4-oxo-5-cyclopentylamino-1,6-naphthyridine (Compound 40),
3-(4-Ethoxyphenyl)-1,4-dihydro-1-methyl-4-oxo-5-phenylamino-1,6-naphthyridine (Compound 41),
3-(4-Ethoxyphenyl)-1,4-dihydro-1-methyl-4-oxo-5-(4-chlorophenylamino)-1,6-naphthyridine (Compound 42),
3-(4-Ethoxyphenyl)-1,4-dihydro-1-methyl-4-oxo-5-(3-pyridylamino)-1,6-naphthyridine (Compound 43);
3-(4-Methoxyphenyl)-1,4-dihydro-1-ethyl-4-oxo-5-phenylamino-1,6-naphthyridine (Compound 44),
3-(4-Trifluoromethylphenyl)-1,4-dihydro-4-oxo-5-(4-chlorophenylamino)-1,6-naphthyridine (Compound 45),
3-(4-Trifluoromethylphenyl)-1,4-dihydro-4-oxo-5-phenylamino-1,6-naphthyridine (Compound 46),
3-(4-Chlorophenyl)-1,4-dihydro-4-oxo-5-(2-chlorophenylamino)-1,6-naphthyridine (Compound 47),
3-(4-Fluorophenyl)-1,4-dihydro-4-oxo-5-(4-chlorophenylamino)-1,6-naphthyridine (Compound 48),
3-(4-Chlorophenyl)-1,4-dihydro-4-oxo-5-(2-phenethylamino)-1,6-naphthyridine (Compound 49),
3-(4-Chlorophenyl)-1,4-dihydro-1-methyl-4-oxo-5-(2-phenethylamino)-1,6-naphthyridine (Compound 50) and
3-(4-Chlorophenyl)-1,4-dihydro-4-oxo-5-(3-chlorophenylamino)-1,6-naphthyridine (Compound 51).

In one aspect, there is provided pharmaceutical compositions comprising a compound of Formula I, II, IIa, III, or IV. In another aspect, there is provided a method for the treatment of disorders amenable to modulation of the α7nAChR comprising administering to a patient in need of such treatment a compound of Formula I, II, IIa, III, or IV or a pharmaceutically acceptable salt, ester, solvate or prodrug thereof. In one embodiment, the disorder is a neurodegenerative disorder. In another embodiment, the disorder is a senile dementia. In another embodiment, the disorder is schizophrenia. In another embodiment, the disorder is a cognition deficit disorder. In another embodiment, the disorder is Alzheimer's disease. In another embodiment, the disorder is related to learning. In another embodiment, the disorder is selected from the group consisting of memory loss, Lewy Body dementia, attention-deficit disorder, attention deficit hyperactivity disorder, anxiety, mania, manic depression, Parkinson's disease, Huntington's disease, amyotrophic lateral sclerosis, brain inflammation and Tourette's syndrome. In another embodiment, the disorder is pain, inflammation, septic shock, ulcerative colitis or irritable bowel syndrome.

In another aspect, there is provided a method for the treatment of a cognitive disorder related to learning and memory comprising administering to a patient in need of such treatment a compound of Formula I, II, IIa, III, or IV or a pharmaceutically acceptable salt, ester, solvate or prodrug thereof. In one embodiment, the cognitive disorder is mild cognitive impairment, age related cognitive decline, senile dementia or Alzheimer's disease. In one embodiment the treatment of such disorders is achieved via modulation of mono and divalent cation conductance through the site mediating the action of a compound of Formula I, II, IIa, III, or IV. In yet another aspect, there is provided a method for the treatment of disorders which comprises administering to a patient in need of such treatment a compound of Formula I, II, IIa, III, or IV or a pharmaceutically acceptable salt thereof. In one embodiment, the compound of Formula I, II, IIa, III, or IV or a pharmaceutically acceptable salt thereof has activity to positively allosterically modulate currents at α7nAChR. Administration of allosteric modulators described herein treating, controlling, ameliorating or reducing the risk of a disorder amenable to modulation of α7nAChR.

For use in medicine, the salts of the compounds of Formula I, II, IIa, III, or IV will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid; tartaric acid, or phosphoric acid. Furthermore, where the compounds comprises an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Standard methods for the preparation of pharmaceutically acceptable salts and their formulations are well known in the art, and are disclosed in various references, including for example, "*Remington: The Science and Practice of Pharmacy*", A. Gennaro, ed., 20$^{th}$ edition, Lippincott, Williams & Wilkins, Philadelphia, Pa.

The present invention includes prodrugs of the compounds of Formula I, II, IIa, III, or IV above. In general, such prodrugs will be functional derivatives of these compounds that are readily convertible in vivo into the required compound of Formula I, II, IIa, III, or IV. Conventional procedures for the selection and preparation of suitable prodrug derivatives are described, for example, in "*Design of Prodrugs*", ed. H. Bundgaard, Elsevier, 1985. Such prodrugs include but are not limited to ester prodrugs from alcohols and acids as well as phosphate prodrugs of alcohols, all of which are familiar to those of skill in the art. The prodrug can be formulated to achieve a goal of improved chemical stability, improved patient acceptance and compliance, improved bioavailability, prolonged duration of action, improved organ selectivity, improved formulation (e.g., increased hydrosolubility), and/or decreased side effects (e.g., toxicity).

Where the compounds of the present invention have at least one asymmetric center, they may accordingly exist as enantiomers. Where the compounds possess two or more asymmetric centers, they may additionally exist as diastereoisomers. It is to be understood that all such stereoisomers and mixtures thereof in any proportion are encompassed within the scope of the present invention. Where the compounds possess geometrical isomers, all such isomers and mixtures thereof in any proportion are encompassed within the scope of the present invention.

Tautomers of the compounds of the invention are encompassed by the present application. Thus, for example, a carbonyl includes its hydroxyl tautomer.

EXAMPLES

Standard procedures and chemical transformation and related methods are well known to one skilled in the art, and such methods and procedures have been described, for example, in standard references such as *Fiesers' Reagents for Organic Synthesis*, John Wiley and Sons, New York, N.Y., 2002; *Organic Reactions*, vols. 1-83, John Wiley and Sons, New York, N.Y., 2006; March J. and Smith M., *Advanced Organic Chemistry*, 6th ed., John Wiley and Sons, New York, N.Y.; and Larock R. C., *Comprehensive Organic Transfor-* mations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, *Protecting Groups in Organic Synthesis,* 3rd edition, John Wiley & Sons, Inc. 1999.

Compounds of Formula III' can be prepared as shown in Scheme 1, starting with commercially available 2,4-dichloropyridines of formula A. Treatment of an appropriately substituted 2,4-dichloropyridine of formula A with a base such as lithium diisopropylamide in THF at −65° C. to −78° C. followed by addition of $CO_2$ and acidification upon workup provides the corresponding nicotinic acid of formula B which is further converted to the acid chloride by oxalyl chloride treatment (cf Dai, *Bioorg. Med. Chem. Lett.* 2008, 18, 386-390). Condensation with an appropriately substituted phenyl acetate yields a β-ketoester which is decarboxylated at elevated temperature to give the desired compounds of formula C (cf Perner, *J. Med. Chem.,* 2003, 46, 5249-5256). Condensation with ethyl formate (Becalli, *J. Org. Chem.* 1984, 49, 4287-4290) followed by regioselective ring closure under basic conditions provides the compounds of formula E (cf Burgart, Mendeleev Communications, 2001, 76). Further reaction with an appropriate amine leads to molecules of Formula III' (cf Giannouli, *J. Med. Chem.,* 2007, 50, 1716-1719).

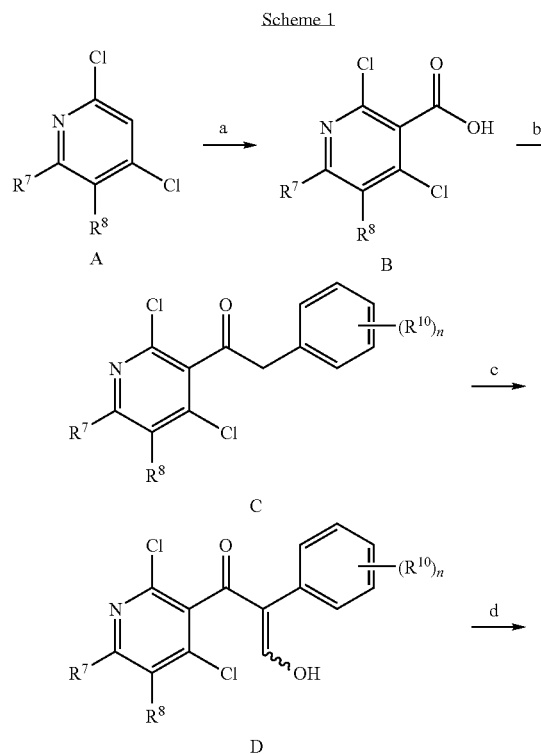

Scheme 1

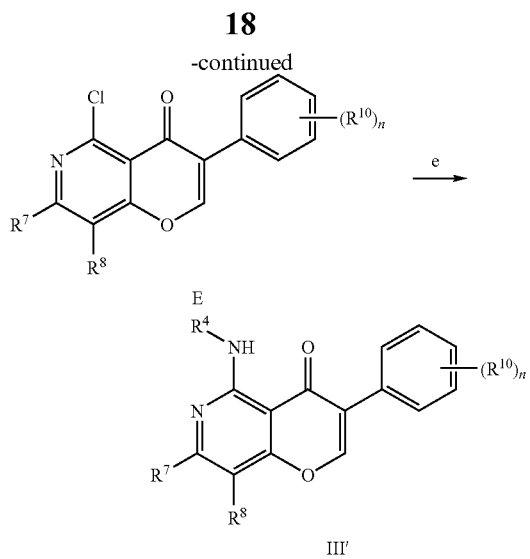

Reagents/Solvents: a. LDA, THF, -78° C.; then $CO_2$ b. (i) Oxalyl chloride, cat. DMF, $CH_2Cl_2$ (ii) LDA, THF, 4-chlorophenyl acetic acid methyl ester (iii) DMSO/$H_2O$, 150° C. c. Ethyl formate, NaH. d. NaH, THF. e. $R^4NH_2$, DMSO, 125° C.

Compounds of Formula IV' can be prepared as shown in Scheme 2, starting with compounds of formula C. Condensation with dimethylformamide dimethyl acetal followed by treatment with hydrogen sulfide provides compounds of formula E' (cf Wentland, *J. Med. Chem.,* 1993, 36, 2801-2809). Further reaction with an appropriate amine leads to compounds of formula IV' (cf Croisy-Delcet, *Heterocycles,* 1991, 32, 1933-1945).

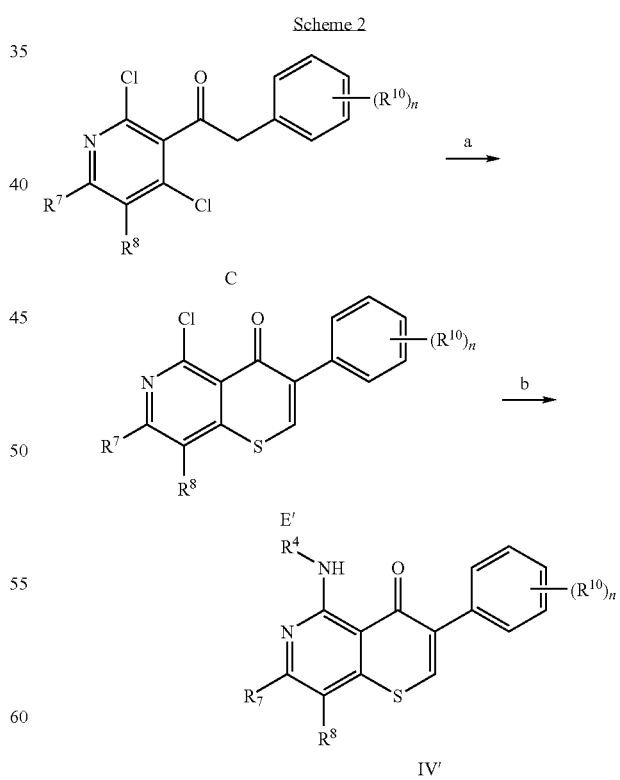

Reagents/Solvents: a. (i) $(MeO)_2CHNMe_2$ (ii) $H_2S$, EtOH. B. $R^4NH_2$, DMSO, 125° C.

Compounds of Formula IIA' were prepared as shown in Scheme 3, starting with ethyl or methyl phenylacetates. The esters are commercially available or were prepared from the corresponding phenylacetic acid using well known literature methods (e.g. EtOH or MeOH/H$_2$SO$_4$). Reaction of the ethyl phenylacetates with ethyl formate was carried out according to the procedure of Beccalli, et al. *J. Org. Chem.* 1984, 49, 4287-4290, to give a hydroxymethylene intermediate. Reaction with a 2-chloro-4-aminopyridine then afforded the desired condensation product, which was cyclized in refluxing phenyl ether to give E'. Addition of an amine R$^4$NH$_2$ in DMSO with heating then gave the desired compound of Formula IIA'.

tions, oocytes were maintained at 16-17° C. in Barth's medium. Two-electrode voltage clamp recordings were made 3-14 days following mRNA injections at a holding voltage of –70 mV unless specified. The nicotinic recordings were done in Ca$^{++}$-free Ringer solution (mM: NaCl, 115; KCl, 2; BaCl$_2$, 1.8; HEPES, 5; pH 7.4) to limit Ca$^{++}$-activated chloride and muscarinic currents. Drug and wash solutions were applied using a microcapillary "linear array" (Hawkinson et al., *Mol. Pharmacol.* 49: 897-906, 1996) in order to allow rapid application of agonists. Currents were recorded on a chart recorder and/or PC-based computer for subsequent analysis. Test com-

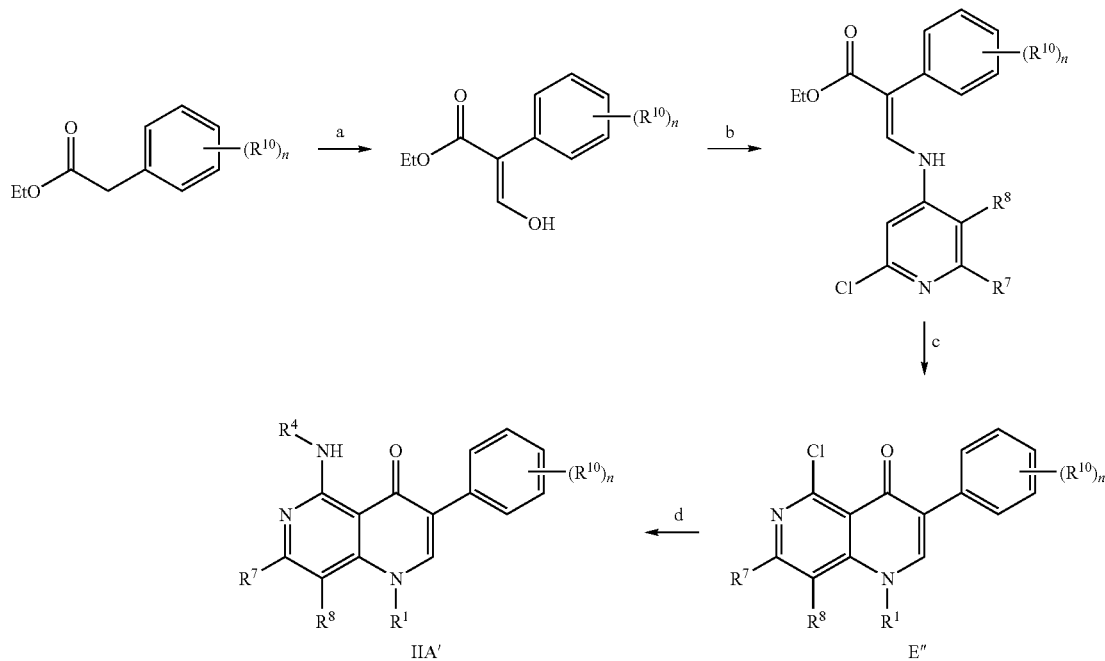

Reagents/Solvents: a. Ethyl formate, NaH. b. aminopyridine/EtOH, reflux. c. PhOPh, reflux. d. R$^4$NH$_2$, DMSO, 125° C.

OOCYTE ELECTROPHYSIOLOGY: Individual compounds were tested for modulation of submaximal nicotine-evoked currents at α7nAChRs using oocytes expressing human receptors. For each oocyte, the maximal nicotine-evoked currents were determined in response to 3 mM nicotine. All other currents were scaled to this value. The concentration of nicotine was adjusted to evoke a fractional current of approximately 0.05 (5% of max, or "EC$_5$"), and this concentration of nicotine was used to generate EC$_5$ control currents. Increasing concentrations of test compounds were applied to oocytes alone (pretreatment) and then in combination with the EC$_5$ concentration of nicotine (co-application). This protocol allowed measurement of both direct effects of test compounds on α7nAChRs, and modulatory effects of compounds on nicotine-evoked responses. mRNA was prepared and stored using conventional techniques from cDNA clones encoding the human nicotinic receptor subunits. Preparation, micro-injection and maintenance of oocytes were performed as reported in detail previously (Whittemore et al., *Mol. Pharmacol.* 50: 1364-1375, 1996). Individual oocytes were injected with 5-50 ng of each subunit mRNA. For multiple subunit combinations, the mRNA ratios are: (1) α4β2 and α3β4 nAChRs (a 1:1 mixture); following injecpounds were made up in DMSO over a concentration range of 0.001-10 mM and diluted 1000-3000-fold into the appropriate saline just prior to testing (final [DMSO]<0.1%). The concentration-dependence of modulation was analyzed using GraphPad "Prism" curve-fitting software. Compounds of the present invention show at least 100% modulation of the nicotine EC$_5$ at 10 µM.

The compounds of the present invention exhibit either at least 100% positive modulation or from 10% to 50% negative modulation of the nicotine EC$_5$ at 10 µM. Certain compounds of the present invention exhibit at least 500% positive modulation of the nicotine EC$_5$ at 10 µM.

Positive allosteric modulators can also be assayed by imaging of calcium flux through α7nAChR transiently expressed in a cell line, including HEK-293 and cell cultured neurons (see for example WO 2006/071184). Activation of native α7nAChRs, by electrophysiological recordings in rat hippocampal slices can also be used to measure the effect of allosteric modulators. The effect can be observed on the activation of α7nAChR mediated currents in hippocampal CA1 stratum radiatum interneurons by the application of ACh in the presence of an allosteric modulator.

Example 1

3-(4-Chlorophenyl)-1,4-dihydro-4-oxo-5-(2-phenethylamino)-1,6-naphthyridine

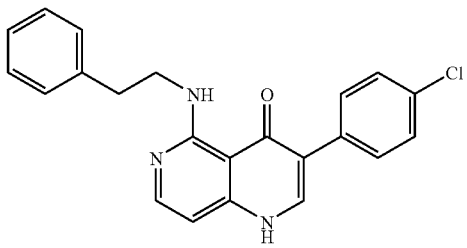 [SMILES: O=c1c(-c2ccc(Cl)cc2)c[nH]c2ccnc(NCCc3ccccc3)c12]

Ethyl α-[[(2-chloro-4-pyridinyl)amino]methylene]-(4-chlorophenyl)acetate. A solution of ethyl (4-chlorophenyl)acetate (10.87 g, 54.72 mmol) in 90 mL of ethyl formate was treated with a 60% suspension of NaH in oil (7.0 g, 175 mmol) added in portions. After stirring overnight, the reaction was added to 130 mL of 10% aq. HCl and 70 mL of water. The resulting mixture was extracted with EtOAc (3×50 mL). The pooled EtOAc layers were washed with water and brine, dried ($Na_2SO_4$), filtered and concentrated. The residue was treated with solid 4-amino-2-chloropyridine (7.08 g) and 100 mL of EtOH. After 48 h at reflux, the reaction was allowed to cool to room temperature. After standing overnight, the precipitate that formed by isolated and washed with EtOH, affording 8.0 g of the desired product.

5-Chloro-3-(4-chlorophenyl)-1,4-dihydro-4-oxo-1,6-naphthyridine. Solid ethyl α-[[(2-chloro-4-pyridinyeamino]methylene]-(4-chlorophenyl)acetate (4.0 g) was added in portions to refluxing phenylether (50 mL). After 20 min at reflux, the reaction was allowed to cool and diluted with hexanes. The precipitate that formed was collected and washed with hexanes. Purification by preparative RPHPLC gave the title compound as a light yellow solid.

3-(4-Chlorophenyl)-1,4-dihydro-4-oxo-5-(2-phenethylamino)-1,6-naphthyridine. A solution of 5-chloro-3-(4-chlorophenyl)-1,4-dihydro-4-oxo-1,6-naphthyridine (158 mg, 0.545 mmol) and phenethylamine (350 µL) in 2 mL of DMSO was heated at 125° C. for 1 h. Purification by preparative HPLC gave the title compound as a light yellow solid. MS 376 $(M+1)^+$.

The following compounds were prepared by using the procedure described above:

3-(4-Chlorophenyl)-1,4-dihydro-4-oxo-5-(2-pyridylmethylamino)-1,6-naphthyridine. The title compound was prepared as described in Example 1 above except that phenethylamine was replaced with 2-(aminomethyl)pyridine. MS 363 $(M+1)^+$.

3-(4-Chlorophenyl)-1,4-dihydro-4-oxo-5-(4-pyridylmethylamino)-1,6-naphthyridine. The title compound was prepared as described in Example 1 above except that phenethylamine was replaced with 4-(aminomethyl)pyridine. MS 363 $(M+1)^+$.

3-(4-Chlorophenyl)-1,4-dihydro-4-oxo-5-phenylamino-1,6-naphthyridine. The title compound was prepared as described in Example 1 above except that phenethylamine was replaced with aniline. MS 348 $(M+1)^+$.

3-(4-Chlorophenyl)-1,4-dihydro-4-oxo-5-propylamino-1,6-naphthyridine. The title compound was prepared as described in Example 1 above except that phenethylamine was replaced with propylamine. MS 314 $(M+1)^+$.

3-(4-Chlorophenyl)-1,4-dihydro-4-oxo-5-benzylamino-1,6-naphthyridine. The title compound was prepared as described in Example 1 above except that phenethylamine was replaced with benzylamine. MS 362 $(M+1)^+$.

3-(4-Chlorophenyl)-1,4-dihydro-4-oxo-5-cyclopropylamino-1,6-naphthyridine. The title compound was prepared as described in Example 1 above except that phenethylamine was replaced with cyclopropylamine. MS 312 $(M+1)^+$.

3-(4-Chlorophenyl)-1,4-dihydro-4-oxo-5-cyclopentylamino-1,6-naphthyridine. The title compound was prepared as described in Example 1 above except that phenethylamine was replaced with cyclopentylamine. MS 340 $(M+1)^+$.

3-(4-Chlorophenyl)-1,4-dihydro-4-oxo-5-cyclopropylmethylamino-1,6-naphthyridine. The title compound was prepared as described in Example 1 above except that phenethylamine was replaced with cyclopropylmethylamine. MS 326 $(M+1)^+$.

3-(4-Chlorophenyl)-1,4-dihydro-4-oxo-5-ethylamino-1,6-naphthyridine. The title compound was prepared as described in Example 1 above except that phenethylamine was replaced with ethylamine. MS 300 $(M+1)^+$.

3-(4-Chlorophenyl)-1,4-dihydro-4-oxo-5-(4-fluorophenylamino)-1,6-naphthyridine. The title compound was prepared as described in Example 1 above except that phenethylamine was replaced with 4-fluoroaniline. MS 366 $(M+1)^+$.

3-(4-Chlorophenyl)-1,4-dihydro-4-oxo-5-(4-chlorophenylamino)-1,6-naphthyridine. The title compound was prepared as described in Example 1 above except that phenethylamine was replaced with 4-chloroaniline. MS 382 $(M+1)^+$.

3-(4-Chlorophenyl)-1,4-dihydro-4-oxo-5-tert-butylamino)-1,6-naphthyridine. The title compound was prepared as described in Example 1 above except that phenethylamine was replaced with tert-butylamine. MS 328 $(M+1)^+$.

3-(4-Chlorophenyl)-1,4-dihydro-4-oxo-5-cyclohexylmethylamino)-1,6-naphthyridine. The title compound was prepared as described in Example 1 above except that phenethylamine was replaced with cyclohexylmethylamine. MS 368 $(M+1)^+$.

3-(4-Chlorophenyl)-1,4-dihydro-4-oxo-5-methylamino-1,6-naphthyridine. The title compound was prepared as described in Example 1 above except that phenethylamine was replaced with methylamine. MS 286 $(M+1)^+$.

3-(4-Methoxyphenyl)-1,4-dihydro-4-oxo-5-phenylamino-1,6-naphthyridine. The title compound was prepared as described in Example 1 above except that ethyl (4-chlorophenyl)acetate was replaced with ethyl (4-methoxyphenyl)acetate and phenethylamine was replaced with aniline. MS 378 $(M+1)^+$.

3-(4-Ethoxyphenyl)-1,4-dihydro-4-oxo-5-phenethylamino-1,6-naphthyridine. The title compound was prepared as described in Example 1 above except that ethyl (4-chlorophenyl)acetate was replaced with ethyl (4-ethoxyphenyl)acetate. MS 386 $(M+1)^+$.

3-(4-Ethoxyphenyl)-1,4-dihydro-4-oxo-5-phenylamino-1,6-naphthyridine. The title compound was prepared as described in Example 1 above except that ethyl (4-chlorophenyl)acetate was replaced with ethyl (4-ethoxyphenyl)acetate and phenethylamine was replaced with aniline. MS 358 $(M+1)^+$.

3-(4-Ethoxyphenyl)-1,4-dihydro-4-oxo-5-benzylamino-1,6-naphthyridine. The title compound was prepared as described in Example 1 above except that ethyl (4-chlorophenyl)acetate was replaced with ethyl (4-ethoxyphenyl)acetate and phenethylamine was replaced with benzylamine. MS 372 $(M+1)^+$.

3-(4-Ethoxyphenyl)-1,4-dihydro-4-oxo-5-cyclohexylmethylamino-1,6-naphthyridine. The title compound was prepared as described in Example 1 above except that ethyl (4-chlorophenyl)acetate was replaced with ethyl (4-ethoxyphenyl)acetate and phenethylamine was replaced with cyclohexylmethylamine. MS 378 (M+1)⁺.

3-(4-Ethoxyphenyl)-1,4-dihydro-4-oxo-5-ethylamino-1,6-naphthyridine. The title compound was prepared as described in Example 1 above except that ethyl (4-chlorophenyl)acetate was replaced with ethyl (4-ethoxyphenyl)acetate and phenethylamine was replaced with ethylamine. MS 310 (M+1)⁺.

3-(4-Ethoxyphenyl)-1,4-dihydro-4-oxo-5-cyclopropylamino-1,6-naphthyridine. The title compound was prepared as described in Example 1 above except that ethyl (4-chlorophenyl)acetate was replaced with ethyl (4-ethoxyphenyl)acetate and phenethylamine was replaced with cyclopropylamine. MS 322 (M+1)⁺.

3-(4-Ethoxyphenyl)-1,4-dihydro-4-oxo-5-cyclopropylmethylamino-1,6-naphthyridine. The title compound was prepared as described in Example 1 above except that ethyl (4-chlorophenyl)acetate was replaced with ethyl (4-ethoxyphenyl)acetate and phenethylamine was replaced with cyclopropylmethylamine. MS 336 (M+1)⁺.

3-(4-Ethoxyphenyl)-1,4-dihydro-4-oxo-5-cyclobutylamino-1,6-naphthyridine. The title compound was prepared as described in Example 1 above except that ethyl (4-chlorophenyl)acetate was replaced with ethyl (4-ethoxyphenyl)acetate and phenethylamine was replaced with cyclobutylamine. MS 336 (M+1)⁺.

3-(4-Ethoxyphenyl)-1,4-dihydro-4-oxo-5-propylamino-1,6-naphthyridine. The title compound was prepared as described in Example 1 above except that ethyl (4-chlorophenyl)acetate was replaced with ethyl (4-ethoxyphenyl)acetate and phenethylamine was replaced with propylamine. MS 324 (M+1)⁺.

3-(4-Ethoxyphenyl)-1,4-dihydro-4-oxo-5-cyclopentylamino-1,6-naphthyridine. The title compound was prepared as described in Example 1 above except that ethyl (4-chlorophenyl)acetate was replaced with ethyl (4-ethoxyphenyl)acetate and phenethylamine was replaced with cyclopentylamine. MS 350 (M+1)⁺.

3-(4-Ethoxyphenyl)-1,4-dihydro-4-oxo-5-amino-1,6-naphthyridine. The title compound was prepared as described in Example 1 above except that ethyl (4-chlorophenyl)acetate was replaced with ethyl (4-ethoxyphenyl)acetate and phenethylamine was replaced with ammonia. MS 282 (M+1)⁺.

3-(p-Tolyl)-1,4-dihydro-4-oxo-5-phenethylamino-1,6-naphthyridine. The title compound was prepared as described in Example 1 above except that ethyl (4-chlorophenyl)acetate was replaced with ethyl (4-tolyl)acetate. MS 356 (M+1)⁺.

3-(4-Trifluoromethylphenyl)-1,4-dihydro-4-oxo-5-(4-chlorophenylamino)-1,6-naphthyridine The title compound was prepared as described in Example 1 above except that ethyl (4-chlorophenyl)acetate was replaced with ethyl (4-trifluoromethyl-phenyl)acetate and phenethylamine was replaced with 4-chloroaniline. MS 416 (M+1)⁺.

3-(4-Trifluoromethylphenyl)-1,4-dihydro-4-oxo-5-phenylamino-1,6-naphthyridine The title compound was prepared as described in Example 1 above except that ethyl (4-chlorophenyl)acetate was replaced with ethyl (4-trifluoromethyl-phenyl)acetate and phenethylamine was replaced with aniline. MS 382 (M+1)⁺.

3-(4-Chlorophenyl)-1,4-dihydro-4-oxo-5-(2-chlorophenylamino)-1,6-naphthyridine The title compound was prepared as described in Example 1 above except that phenethylamine was replaced with 2-chloroaniline. MS 382 (M+1)⁺.

3-(4-Chlorophenyl)-1,4-dihydro-4-oxo-5-(3-chlorophenylamino)-1,6-naphthyridine The title compound was prepared as described in Example 1 above except that phenethylamine was replaced with 3-chloroaniline. MS 382 (M+1)⁺.

3-(4-Fluorophenyl)-1,4-dihydro-4-oxo-5-(4-chlorophenylamino)-1,6-naphthyridine The title compound was prepared as described in Example 1 above except that ethyl (4-chlorophenyl)acetate was replaced with ethyl (4-fluorophenyl)acetate and phenethylamine was replaced with 4-chloroaniline. MS 366 (M+1)⁺.

Example 2

3-(4-Chlorophenyl)-1,4-dihydro-1-methyl-4-oxo-5-(2-phenethylamino)-1,6-naphthyridine

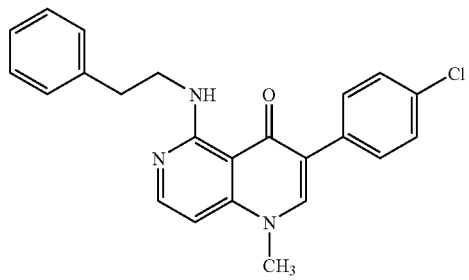 [SMILES: Cn1cc(-c2ccc(Cl)cc2)c(=O)c2c(NCCc3ccccc3)nccc21]

A solution of 3-(4-chlorophenyl)-1,4-dihydro-4-oxo-5-(2-phenethylamino)-1,6-naphthyridine (57 mg, 0.15 mmol) in 2 mL of DMF was treated with solid K₂CO₃ (21 mg) and iodomethane (10 μL). After stirring overnight, the title compound was isolated by preparative RPHPLC. MS 390 (M+1)⁺.

The following compounds were prepared by using the procedure described above:

3-(4-Chlorophenyl)-1,4-dihydro-1-benzyl-4-oxo-5-benzylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-chlorophenyl)-1,4-dihydro-4-oxo-5-benzylamino-1,6-naphthyridine and iodomethane was replaced with benzyl chloride. MS 462 (M+1)⁺.

3-(4-Chlorophenyl)-1,4-dihydro-1-cyclopropylmethyl-4-oxo-5-benzylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-chlorophenyl)-1,4-dihydro-4-oxo-5-benzylamino-1,6-naphthyridine and iodomethane was replaced with cyclopropylmethyl bromide. MS 426 (M+1)⁺.

3-(4-Chlorophenyl)-1,4-dihydro-1-butyl-4-oxo-5-benzylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-chlorophenyl)-1,4-dihydro-4-oxo-5-benzylamino-1,6-naphthyridine and iodomethane was replaced with iodobutane. MS 428 (M+1)⁺.

3-(4-Ethoxyphenyl)-1,4-dihydro-1-methyl-4-oxo-5-phenethylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-(2-phenethylamino)-1,6-naphthyridine. MS 400 (M+1)⁺.

3-(4-Ethoxyphenyl)-1,4-dihydro-1-methyl-4-oxo-5-benzylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-benzylamino-1,6-naphthyridine. MS 387 $(M+1)^+$.

3-(4-Ethoxyphenyl)-1,4-dihydro-1-methyl-4-oxo-5-cyclohexylmethylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-cyclohexylmethylamino-1,6-naphthyridine. MS 393 $(M+1)^+$.

3-(4-Ethoxyphenyl)-1,4-dihydro-1-ethyl-4-oxo-5-phenethylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-(2-phenethylamino)-1,6-naphthyridine and iodomethane was replaced with iodoethane. MS 414 $(M+1)^+$.

3-(4-Ethoxyphenyl)-1,4-dihydro-1-methyl-4-oxo-5-propylamino-1,6-naphthyridine. The title compound was prepared as described in Example 2 above except that 3-4-chlorophenyl)-1,4-dihydro-4-oxo-5-(2-phenethylamino)-1,6-naphthyridine was replaced with 3-(4-ethoxyphenyl)-1,4-dihydro-4-oxo-5-propylamino-1,6-naphthyridine. MS 338 $(M+1)^+$.

3-(4-Ethoxyphenyl)-1,4-dihydro-1-methyl-4-oxo-5-cyclobutylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-cyclobutylamino-1,6-naphthyridine. MS 350 $(M+1)^+$.

3-(4-Ethoxyphenyl)-1,4-dihydro-1-methyl-4-oxo-5-ethylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-ethylamino-1,6-naphthyridine. MS 324 $(M+1)^+$.

3-(4-Ethoxyphenyl)-1,4-dihydro-1-methyl-4-oxo-5-cyclopropylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-cyclopropylamino-1,6-naphthyridine. MS 336 $(M+1)^+$.

3-(4-Ethoxyphenyl)-1,4-dihydro-1-methyl-4-oxo-5-cyclopropylmethylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-cyclopropylmethylamino-1,6-naphthyridine. MS 350 $(M+1)^+$.

3-(4-Ethoxyphenyl)-1,4-dihydro-1-methyl-4-oxo-5-cyclopentylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-cyclopentylamino-1,6-naphthyridine. MS 364 $(M+1)^+$.

3-(4-Ethoxyphenyl)-1,4-dihydro-1-methyl-4-oxo-5-phenylamino-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-phenylamino-1,6-naphthyridine. MS 372 $(M+1)^+$.

3-(4-Ethoxyphenyl)-1,4-dihydro-1-methyl-4-oxo-5-(4-chlorophenylamino)-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-(4-chlorophenylamino)-1,6-naphthyridine. MS 406 $(M+1)^+$.

3-(4-Ethoxyphenyl)-1,4-dihydro-1-methyl-4-oxo-5-(3-pyridylamino)-1,6-naphthyridine. The title compound was prepared as described in Example 2 above except that 3-(4-chlorophenyl)-1,4-dihydro-4-oxo-5-(2-phenethylamino)-1,6-naphthyridine was replaced with 3-(4-ethoxyphenyl)-1,4-dihydro-4-oxo-5-(3-pyridylamino)-1,6-naphthyridine. MS 373 $(M+1)^+$.

3-(4-Methoxyphenyl)-1,4-dihydro-1-ethyl-4-oxo-5-phenylamino-1,6-naphthyridine The title compound was prepared as described in Example 2 above except that 3-(4-chlorophenyl)-1,4-dihydro-4-oxo-5-(2-phenethylamino)-1,6-naphthyridine was replaced with 3-(4-methoxyphenyl)-1,4-dihydro-4-oxo-5-phenylamino-1,6-naphthyridine and iodomethane was replaced with iodoethane. MS 372 $(M+1)^+$.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

What is claimed is:
1. A compound of Formula I:

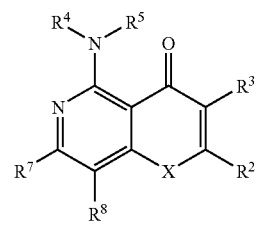

or a pharmaceutically acceptable salt or solvate thereof, wherein:
X is N—$R^1$;
$R^1$ is hydrogen, $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or
$R^1$ is aryl, heteroaryl, cycloalkyl, cycloalkenyl, heterocycloalkyl or heterocycloalkenyl, wherein said heterocycloalkyl is optionally fused with phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^2$ is hydrogen, halogen, nitrile, nitro or —C(=O)$R^9$; or $R^2$ is $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^2$ is aryl, carbon-attached heteroaryl, cycloalkyl, cycloalkenyl, carbon-attached heterocycloalkyl or carbon-attached heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^3$ is aryl, heteroaryl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^4$ is hydrogen, $C_{1-6}$ alkyl, $C_{2-6}$ alkenyl, $C_{2-6}$ alkynyl, or $C_{1-8}$ haloalkyl, wherein each of said alkyl, alkenyl, alkynyl, and haloalkyl is optionally substituted with one or more $R^9$; or $R^4$ is aryl, heteroaryl, cycloalkyl, cycloalkenyl, heterocycloalkyl or heterocycloalkenyl, wherein heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^5$ is hydrogen, $C_{1-6}$ alkyl, $C_{2-6}$ alkenyl, $C_{2-6}$ alkynyl, $C_{1-6}$ haloalkyl, —C(=O)$R^9$, —S(=O)$_{0-2}R^9$, —S(=O)$_{0-2}$-A-$R^9$ or -A-C(=O)$R^9$, wherein each of said alkyl, alkenyl, alkynyl, and haloalkyl is optionally substituted with one or more $R^9$; or $R^5$ is aryl, heteroaryl, cycloalkyl, cycloalkenyl, heterocycloalkyl or heterocycloalkenyl, wherein said heterocycloalkyl is optionally fused with a phenyl or a 5-6 membered heteroaryl, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$; or $R^4$ and $R^5$ taken together with the nitrogen to which they are attached form a heteroaryl, a heterocycloalkyl or a heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said heteroaryl, heterocycloalkyl, and heterocycloalkenyl is optionally substituted with 1-5$R^{10}$;

each of $R^7$ and $R^8$ is independently hydrogen, $C_{1-8}$ alkyl, $C_{1-8}$ alkoxy, $C_{2-8}$ alkenyl, $C_{2-8}$ alkynyl, $C_{1-8}$ haloalkyl, or $C_{1-8}$ haloalkoxy; wherein each of said alkyl, alkenyl, alkynyl, haloalkyl, and haloalkoxy is optionally substituted with one or more $R^9$; or each of $R^7$ and $R^8$ is independently halogen, nitrile, nitro, hydroxyl, —C(=O)$R^9$, —S(=O)$_{0-2}R^9$, —NR$^4$R$^5$, —O-A-$R^9$, —S(=O)$_{0-2}$-A-$R^9$ or -A-C(=O)$R^9$; or each of $R^7$ and $R^8$ is independently aryl, heteroaryl, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$; or $R^9$ is hydroxyl, $C_{1-6}$ alkoxy, $C_{1-8}$ haloalkoxy, $C_{3-6}$ cycloalkoxy or —NR$^{11}$R$^{12}$; or $R^9$ is aryl, heteroaryl, cycloalkyl, or cycloalkenyl, wherein each of said aryl, heteroaryl, cycloalkyl and cycloalkenyl are optionally substituted with 1-5 $R^{10}$; or $R^9$ is heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said heterocycloalkyl and said heterocycloalkenyl is optionally substituted with 1-5 $R^{10}$;

$R^{10}$ is nitro, nitrile, hydroxyl, halogen, $C_{1-6}$ acyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cycloalkoxy, cycloalkyloxy, aryl, heteroaryl, —NR$^{11}$R$^{12}$, —C(=O)OR$^{11}$, —C(=O)NHR$^{11}$, —NHC(=O)R$^{13}$, —NHS(=O)$_2$R$^{13}$, —S(=O)$_{0-2}$R$^{13}$, —S(=O)$_2$NHR$^{11}$, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O); wherein each of said alkyl, alkenyl, alkynyl, haloalkyl, alkoxy, haloalkoxy, cycloalkoxy, cycloalkyloxy, aryl, heteroaryl, cycloalkyl, cycloalkenyl, heterocycloalkyl, and heterocycloalkenyl is optionally substituted;

each of $R^{11}$ and $R^{12}$ is independently hydrogen, $C_{1-6}$ alkyl, $C_{2-6}$ alkenyl, $C_{2-6}$ alkynyl, $C_{1-6}$ haloalkyl, cycloalkyl or cycloalkenyl; wherein each of said alkyl, alkenyl, alkynyl, haloalkyl, cycloalkyl and cycloalkenyl is optionally substituted with one or more $R^9$;

$R^{13}$ is $C_{1-6}$ alkyl, $C_{2-6}$ alkenyl, $C_{2-6}$ alkynyl, $C_{1-6}$ haloalkyl, $C_{3-6}$ cycloalkyl or $C_{4-6}$ cycloalkenyl; wherein each of said alkyl, alkenyl, alkynyl, haloalkyl, cycloalkyl and cycloalkenyl is optionally substituted; and A is $C_{1-8}$ alkyl, $C_{2-8}$ alkenyl or $C_{1-8}$ haloalkyl.

2. A compound according to claim 1, wherein $R^1$ is hydrogen, $C_{1-6}$ alkyl, $C_{1-6}$ haloalkyl or $C_{1-6}$ cycloalkyl, wherein each of said $C_{1-6}$ alkyl and $C_{1-6}$ haloalkyl is optionally substituted with one or more $R^9$ and said $C_{1-6}$ cycloalkyl is optionally substituted with 1-5 $R^{10}$, and pharmaceutically acceptable salts thereof.

3. A compound according to claim 1, wherein $R^2$ is hydrogen, $C_{1-6}$ alkyl, $C_{1-6}$ haloalkyl or $C_{1-6}$ cycloalkyl, wherein each of said $C_{1-6}$ alkyl and $C_{1-6}$ haloalkyl is optionally substituted with one or more $R^9$ and said $C_{1-6}$ cycloalkyl is optionally substituted with 1-5 $R^{10}$, and pharmaceutically acceptable salts thereof.

4. A compound according to claim 1, wherein $R^3$ is aryl or heteroaryl, wherein each of said aryl and heteroaryl is optionally substituted with 1-5 $R^{10}$, and pharmaceutically acceptable salts thereof.

5. A compound according to claim 4, wherein $R^3$ is

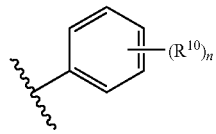

and n is 0-5, and pharmaceutically acceptable salts thereof.

6. A compound according to claim 1, wherein $R^4$ is hydrogen, and pharmaceutically acceptable salts thereof.

7. A compound according to claim 6, wherein $R^5$ is $C_{1-6}$ alkyl optionally substituted with one or more $R^9$, and pharmaceutically acceptable salts thereof.

8. A compound according to claim 1, wherein $R^9$ is aryl, heteroaryl or cycloalkyl, and pharmaceutically acceptable salts thereof.

9. A compound according to claim 1, wherein $R^{10}$ is halogen, $C_{1-6}$ alkyl, $C_{1-6}$ haloalkyl, $C_{1-6}$ alkoxy or cycloalkyloxy, and pharmaceutically acceptable salts thereof.

10. A compound according to claim 1, wherein said compound is:
3-(4-Chlorophenyl)-1,4-dihydro-4-oxo-5-(2-pyridylmethylamino)-1,6-naphthyridine;
3-(4-Chlorophenyl)-1,4-dihydro-4-oxo-5-(4-pyridylmethylamino)-1,6-naphthyridine;
3-(4-Chlorophenyl)-1,4-dihydro-4-oxo-5-phenylamino-1,6-naphthyridine;
3-(4-Chlorophenyl)-1,4-dihydro-4-oxo-5-propylamino-1,6-naphthyridine;
3-(4-Chlorophenyl)-1,4-dihydro-4-oxo-5-benzylamino-1,6-naphthyridine;
3-(4-Chlorophenyl)-1,4-dihydro-4-oxo-5-cyclopropylamino-1,6-naphthyridine;
3-(4-Chlorophenyl)-1,4-dihydro-4-oxo-5-cyclopentylamino-1,6-naphthyridine;
3-(4-Chlorophenyl)-1,4-dihydro-4-oxo-5-cyclopropylmethylamino-1,6-naphthyridine;
3-(4-Chlorophenyl)-1,4-dihydro-4-oxo-5-ethylamino-1,6-naphthyridine;
3-(4-Chlorophenyl)-1,4-dihydro-4-oxo-5-(4-fluorophenylamino)-1,6-naphthyridine;
3-(4-Chlorophenyl)-1,4-dihydro-4-oxo-5-(4-chlorophenylamino)-1,6-naphthyridine;
3-(4-Chlorophenyl)-1,4-dihydro-4-oxo-5-tert-butylamino-1,6-naphthyridine;
3-(4-Chlorophenyl)-1,4-dihydro-4-oxo-5-cyclohexylmethylamino-1,6-naphthyridine;
3-(4-Chlorophenyl)-1,4-dihydro-4-oxo-5-methylamino-1,6-naphthyridine;
3-(4-Methoxyphenyl)-1,4-dihydro-4-oxo-5-phenylamino-1,6-naphthyridine;
3-(4-Ethoxyphenyl)-1,4-dihydro-4-oxo-5-phenethylamino-1,6-naphthyridine;
3-(4-Ethoxyphenyl)-1,4-dihydro-4-oxo-5-phenylamino-1,6-naphthyridine;
3-(4-Ethoxyphenyl)-1,4-dihydro-4-oxo-5-benzylamino-1,6-naphthyridine;
3-(4-Ethoxyphenyl)-1,4-dihydro-4-oxo-5-cyclohexylmethylamino-1,6-naphthyridine;
3-(4-Ethoxyphenyl)-1,4-dihydro-4-oxo-5-ethylamino-1,6-naphthyridine;
3-(4-Ethoxyphenyl)-1,4-dihydro-4-oxo-5-cyclopropylamino-1,6-naphthyridine;
3-(4-Ethoxyphenyl)-1,4-dihydro-4-oxo-5-cyclopropylmethylamino-1,6-naphthyridine;
3-(4-Ethoxyphenyl)-1,4-dihydro-4-oxo-5-cyclobutylamino-1,6-naphthyridine;
3-(4-Ethoxyphenyl)-1,4-dihydro-4-oxo-5-propylamino-1,6-naphthyridine;
3-(4-Ethoxyphenyl)-1,4-dihydro-4-oxo-5-cyclopentylamino-1,6-naphthyridine;
3-(4-Ethoxyphenyl)-1,4-dihydro-4-oxo-5-amino-1,6-naphthyridine;
3-(p-Tolyl)-1,4-dihydro-4-oxo-5-phenethylamino-1,6-naphthyridine;
3-(4-Chlorophenyl)-1,4-dihydro-1-benzyl-4-oxo-5-benzylamino-1,6-naphthyridine;
3-(4-Chlorophenyl)-1,4-dihydro-1-cyclopropylmethyl-4-oxo-5-benzylamino-1,6-naphthyridine;
3-(4-Chlorophenyl)-1,4-dihydro-1-butyl-4-oxo-5-benzylamino-1,6-naphthyridine;
3-(4-Ethoxyphenyl)-1,4-dihydro-1-methyl-4-oxo-5-phenethylamino-1,6-naphthyridine;
3-(4-Ethoxyphenyl)-1,4-dihydro-1-methyl-4-oxo-5-benzylamino-1,6-naphthyridine;
3-(4-Ethoxyphenyl)-1,4-dihydro-1-methyl-4-oxo-5-cyclohexylmethylamino-1,6-naphthyridine;
3-(4-Ethoxyphenyl)-1,4-dihydro-1-ethyl-4-oxo-5-phenethylamino-1,6-naphthyridine;
3-(4-Ethoxyphenyl)-1,4-dihydro-1-methyl-4-oxo-5-propylamino-1,6-naphthyridine;
3-(4-Ethoxyphenyl)-1,4-dihydro-1-methyl-4-oxo-5-cyclobutylamino-1,6-naphthyridine;
3-(4-Ethoxyphenyl)-1,4-dihydro-1-methyl-4-oxo-5-ethylamino-1,6-naphthyridine;
3-(4-Ethoxyphenyl)-1,4-dihydro-1-methyl-4-oxo-5-cyclopropylamino-1,6-naphthyridine;
3-(4-Ethoxyphenyl)-1,4-dihydro-1-methyl-4-oxo-5-cyclopropylmethylamino-1,6-naphthyridine;
3-(4-Ethoxyphenyl)-1,4-dihydro-1-methyl-4-oxo-5-cyclopentylamino-1,6-naphthyridine;
3-(4-Ethoxyphenyl)-1,4-dihydro-1-methyl-4-oxo-5-phenylamino-1,6-naphthyridine;
3-(4-Ethoxyphenyl)-1,4-dihydro-1-methyl-4-oxo-5-(4-chlorophenylamino)-1,6-naphthyridine;
3-(4-Ethoxyphenyl)-1,4-dihydro-1-methyl-4-oxo-5-(3-pyridylamino)-1,6-naphthyridine;
3-(4-Methoxyphenyl)-1,4-dihydro-1-ethyl-4-oxo-5-phenylamino-1,6-naphthyridine;
3-(4-Trifluoromethylphenyl)-1,4-dihydro-4-oxo-5-(4-chlorophenylamino)-1,6-naphthyridine;
3-(4-Trifluoromethylphenyl)-1,4-dihydro-4-oxo-5-phenylamino-1,6-naphthyridine;
3-(4-Chlorophenyl)-1,4-dihydro-4-oxo-5-(2-chlorophenylamino)-1,6-naphthyridine;

3-(4-Fluorophenyl)-1,4-dihydro-4-oxo-5-(4-chlorophenylamino)-1,6-naphthyridine;

3-(4-Chlorophenyl)-1,4-dihydro-4-oxo-5-(2-phenethylamino)-1,6-naphthyridine;

3-(4-Chlorophenyl)-1,4-dihydro-1-methyl-4-oxo-5-(2-phenethylamino)-1,6-naphthyridine; or 3-(4-Chlorophenyl)-1,4-dihydro-4-oxo-5-(3-chlorophenylamino)-1,6-naphthyridine and pharmaceutically acceptable salts thereof.

11. A pharmaceutical composition comprising a pharmaceutically acceptable diluent or carrier and a compound of Formula I:

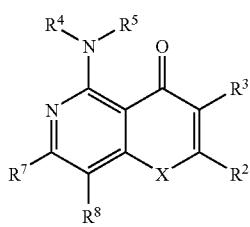

I or a pharmaceutically acceptable salt or solvate thereof, wherein:

X is N—$R^1$;

$R^1$ is hydrogen, $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^1$ is aryl, heteroaryl, cycloalkyl, cycloalkenyl, heterocycloalkyl or heterocycloalkenyl, wherein said heterocycloalkyl is optionally fused with phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^2$ is hydrogen, halogen, nitrile, nitro or —C(═O)$R^9$; or $R^2$ is $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^2$ is aryl, carbon-attached heteroaryl, cycloalkyl, cycloalkenyl, carbon-attached heterocycloalkyl or carbon-attached heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^3$ is aryl, heteroaryl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^4$ is hydrogen, $C_{1-6}$ alkyl, $C_{2-6}$ alkenyl, $C_{2-6}$ alkynyl, or $C_{1-8}$ haloalkyl, wherein each of said alkyl, alkenyl, alkynyl, and haloalkyl is optionally substituted with one or more $R^9$; or $R^4$ is aryl, heteroaryl, cycloalkyl, cycloalkenyl, heterocycloalkyl or heterocycloalkenyl, wherein heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$;

$R^5$ is hydrogen, $C_{1-6}$ alkyl, $C_{2-6}$ alkenyl, $C_{2-6}$ alkynyl, $C_{1-6}$ haloalkyl, —C(═O)$R^9$, —S(═O)$_{0-2}$$R^9$, —S(═O)$_{0-2}$-A-$R^9$ or A-C(═O)$R^9$, wherein each of said alkyl, alkenyl, alkynyl, and haloalkyl is optionally substituted with one or more $R^9$; or $R^5$ is aryl, heteroaryl, cycloalkyl, cycloalkenyl, heterocycloalkyl or heterocycloalkenyl, wherein said heterocycloalkyl is optionally fused with a phenyl or a 5-6 membered heteroaryl, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$; or $R^4$ and $R^5$ taken together with the nitrogen to which they are attached form a heteroaryl, a heterocycloalkyl or a heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said heteroaryl, heterocycloalkyl, and heterocycloalkenyl is optionally substituted with 1-5$R^{10}$;

each of $R^7$ and $R^8$ is independently hydrogen, $C_{1-8}$ alkyl, $C_{1-8}$ alkoxy, $C_{2-8}$ alkenyl, $C_{2-8}$ alkynyl, $C_{1-8}$ haloalkyl, or $C_{1-8}$ haloalkoxy; wherein each of said alkyl, alkenyl, alkynyl, haloalkyl, and haloalkoxy is optionally substituted with one or more $R^9$; or each of $R^7$ and $R^8$ is independently halogen, nitrile, nitro, hydroxyl, —C(═O)$R^9$, —S(═O)$_{0-2}$$R^9$, —NR$^4$R$^5$, —O-A-$R^9$, —S(═O)$_{0-2}$-A-$R^9$ or -A-C(═O)$R^9$; or each of $R^7$ and $R^8$ is independently aryl, heteroaryl, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(═O), wherein each of said aryl, heteroaryl, cycloalkyl, cycloalkenyl, heterocycloalkyl, and heterocycloalkenyl is optionally substituted with 1-5 $R^{10}$; or $R^9$ is hydroxyl, $C_{1-6}$ alkoxy, $C_{1-8}$ haloalkoxy, $C_{3-6}$ cycloalkoxy or —NR$^{11}$R$^{12}$; or $R^9$ is aryl, heteroaryl, cycloalkyl, or cycloalkenyl, wherein each of said aryl, heteroaryl, cycloalkyl and cycloalkenyl are optionally substituted with 1-5 $R^{10}$; or $R^9$ is heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said heterocycloalkyl and said heterocycloalkenyl is optionally substituted with 1-5 $R^{10}$;

$R^{10}$ is nitro, nitrile, hydroxyl, halogen, $C_{1-6}$ acyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cycloalkoxy, cycloalkyloxy, aryl, heteroaryl, —$NR^{11}R^{12}$, —C(=O)$OR^{11}$, —C(=O)$NHR^{11}$, —NHC(=O)$R^{13}$, —NHS(=O)$_2$$R^{13}$, —S(=O)$_{0-2}$$R^{13}$, —S(=O)$_2$$NHR^{11}$, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O); wherein each of said alkyl, alkenyl, alkynyl, haloalkyl, alkoxy, haloalkoxy, cycloalkoxy, cycloalkyloxy, aryl, heteroaryl, cycloalkyl, cycloalkenyl, heterocycloalkyl, and heterocycloalkenyl is optionally substituted;

each of $R^{11}$ and $R^{12}$ is independently hydrogen, $C_{1-6}$ alkyl, $C_{2-6}$ alkenyl, $C_{2-6}$ alkynyl, $C_{1-6}$ haloalkyl, cycloalkyl or cycloalkenyl; wherein each of said alkyl, alkenyl, alkynyl, haloalkyl, cycloalkyl and cycloalkenyl is optionally substituted with one or more $R^9$;

$R^{13}$ is $C_{1-6}$ alkyl, $C_{2-6}$ alkenyl, $C_{2-6}$ alkynyl, $C_{1-6}$ haloalkyl, $C_{3-6}$ cycloalkyl or $C_{4-6}$ cycloalkenyl; wherein each of said alkyl, alkenyl, alkynyl, haloalkyl, cycloalkyl and cycloalkenyl is optionally substituted; and A is $C_{1-8}$ alkyl, $C_{2-8}$ alkenyl or $C_{1-8}$ haloalkyl.

12. A pharmaceutical composition according to claim 11, wherein $R^3$ is

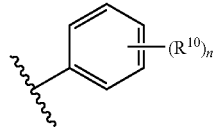

and n is 0-5, and pharmaceutically acceptable salts thereof.

13. A method for treating a disorder selected from the group consisting of senile dementia, schizophrenia, learning deficit, cognition deficit, memory loss, Lewy Body dementia, attention-deficit disorder, attention deficit hyperactivity disorder, anxiety, mania, manic depression, amyotrophic lateral sclerosis, brain inflammation, pain, inflammation, septic shock, ulcerative colitis, and irritable bowel syndrome comprising administering to a patient in need of such treatment an effective amount of a pharmaceutical composition comprising a compound of Formula I:

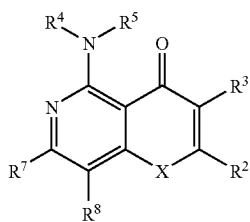

I or a pharmaceutically acceptable salt or solvate thereof, wherein:

X is N—$R^1$;

$R^1$ is hydrogen, $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^1$ is aryl, heteroaryl, cycloalkyl, cycloalkenyl, heterocycloalkyl or heterocycloalkenyl, wherein said heterocycloalkyl is optionally fused with phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^2$ is hydrogen, halogen, nitrile, nitro or —C(=O)$R^9$; or $R^2$ is $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^2$ is aryl, carbon-attached heteroaryl, cycloalkyl, cycloalkenyl, carbon-attached heterocycloalkyl or carbon-attached heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^3$ is aryl, heteroaryl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^4$ is hydrogen, $C_{1-6}$ alkyl, $C_{2-6}$ alkenyl, $C_{2-6}$ alkynyl, or $C_{1-8}$ haloalkyl, wherein each of said alkyl, alkenyl, alkynyl, and haloalkyl is optionally substituted with one or more $R^9$; or $R^4$ is aryl, heteroaryl, cycloalkyl, cycloalkenyl, heterocycloalkyl or heterocycloalkenyl, wherein heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^5$ is hydrogen, $C_{1-6}$ alkyl, $C_{2-6}$ alkenyl, $C_{2-6}$ alkynyl, $C_{1-6}$ haloalkyl, —C(=O)$R^9$, —S(=O)$_{0-2}$$R^9$, —S(=O)$_{0-2}$-A-$R^9$ or -A-C(=O)$R^9$, wherein each of said alkyl, alkenyl, alkynyl, and haloalkyl is optionally substituted with one or more $R^9$; or $R^5$ is aryl, heteroaryl, cycloalkyl, cycloalkenyl, heterocycloalkyl or heterocycloalkenyl, wherein said heterocycloalkyl is optionally fused with a phenyl or a 5-6 membered heteroaryl, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$; or $R^4$ and $R^5$ taken together with the nitrogen to which they are attached form a heteroaryl, a heterocycloalkyl or a heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said heteroaryl, heterocycloalkyl, and heterocycloalkenyl is optionally substituted with 1-5 $R^{10}$;

each of $R^7$ and $R^8$ is independently hydrogen, $C_{1-8}$ alkyl, $C_{1-8}$ alkoxy, $C_{2-8}$ alkenyl, $C_{2-8}$ alkynyl, $C_{1-8}$ haloalkyl, or $C_{1-8}$ haloalkoxy; wherein each of said alkyl, alkenyl, alkynyl, haloalkyl, and haloalkoxy is optionally substituted with one or more $R^9$; or each of $R^7$ and $R^8$ is independently halogen, nitrile, nitro, hydroxyl, —C(=O)$R^9$, —S(=O)$_{0-2}R^9$, —$NR^4R^5$, —O-A-$R^9$, —S(=O)$_{0-2}$-A-$R^9$ or -A-C(=O)$R^9$; or each of $R^7$ and $R^8$ is independently aryl, heteroaryl, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$; or $R^9$ is hydroxyl, $C_{1-6}$ alkoxy, $C_{1-8}$ haloalkoxy, $C_{3-6}$ cycloalkoxy or —$NR^{11}R^{12}$; or $R^9$ is aryl, heteroaryl, cycloalkyl, or cycloalkenyl, wherein each of said aryl, heteroaryl, cycloalkyl and cycloalkenyl are optionally substituted with 1-5 $R^{10}$; or $R^9$ is heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said heterocycloalkyl and said heterocycloalkenyl is optionally substituted with 1-5 $R^{10}$;

$R^{10}$ is nitro, nitrile, hydroxyl, halogen, $C_{1-6}$ acyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cycloalkoxy, cycloalkyloxy, aryl, heteroaryl, —$NR^{11}R^{12}$, —C(=O)$OR^{11}$, —C(=O)$NHR^{11}$, —NHC(=O)$R^{13}$, —NHS(=O)$_2R^{13}$, —S(=O)$_{0-2}R^{13}$, —S(=O)$_2NHR^{11}$, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O); wherein each of said alkyl, alkenyl, alkynyl, haloalkyl, alkoxy, haloalkoxy, cycloalkoxy, cycloalkyloxy, aryl, heteroaryl, cycloalkyl, cycloalkenyl, heterocycloalkyl, and heterocycloalkenyl is optionally substituted;

each of $R^{11}$ and $R^{12}$ is independently hydrogen, $C_{1-6}$ alkyl, $C_{2-6}$ alkenyl, $C_{2-6}$ alkynyl, $C_{1-6}$ haloalkyl, cycloalkyl or cycloalkenyl; wherein each of said alkyl, alkenyl, alkynyl, haloalkyl, cycloalkyl and cycloalkenyl is optionally substituted with one or more $R^9$;

$R^{13}$ is $C_{1-6}$ alkyl, $C_{2-6}$ alkenyl, $C_{2-6}$ alkynyl, $C_{1-6}$ haloalkyl, $C_{3-6}$ cycloalkyl or $C_{4-6}$ cycloalkenyl; wherein each of said alkyl, alkenyl, alkynyl, haloalkyl, cycloalkyl and cycloalkenyl is optionally substituted; and A is $C_{1-8}$ alkyl, $C_{2-8}$ alkenyl or $C_{1-8}$ haloalkyl.

14. A method according to claim 13, wherein $R^3$ is

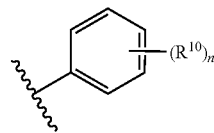

and n is 0-5, and pharmaceutically acceptable salts thereof.

15. A method according to claim 14, wherein said disorder is a cognitive disorder related to learning or memory.

16. A method according to claim 15, wherein said cognitive disorder is mild cognitive impairment, age related cognitive decline, senile dementia or Alzheimer's disease.

17. A method according to claim 13, wherein said disorder is a cognitive disorder related to learning or memory.

18. A method according to claim 17, wherein said cognitive disorder is mild cognitive impairment, age related cognitive decline, senile dementia or Alzheimer's disease.

19. A method for modulating α7nAChR comprising administering to a patient in need of such modulation an effective amount of a pharmaceutical composition comprising a compound of Formula I:

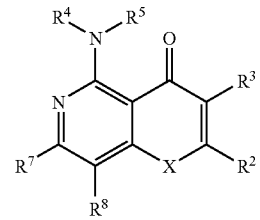

or a pharmaceutically acceptable salt or solvate thereof, wherein:

X is N—$R^1$;

$R^1$ is hydrogen, $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^1$ is aryl, heteroaryl, cycloalkyl, cycloalkenyl, heterocycloalkyl or heterocycloalkenyl, wherein said heterocycloalkyl is optionally fused with phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^2$ is hydrogen, halogen, nitrile, nitro or —C(=O)$R^9$; or $R^2$ is $C_{1-8}$ alkyl, $C_{2-8}$ alkenyl, $C_{2-8}$ alkynyl, or $C_{1-8}$ haloalkyl, wherein each of said alkyl, alkenyl, alkynyl, and haloalkyl is optionally substituted with one or more $R^9$; or $R^2$ is aryl, carbon-attached heteroaryl, cycloalkyl, cycloalkenyl, carbon-attached heterocycloalkyl or carbon-attached heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to C(=O), wherein each of said aryl, heteroaryl, cycloalkyl, cycloalkenyl, heterocycloalkyl, and heterocycloalkenyl is optionally substituted with 1-5 $R^{10}$;

$R^3$ is aryl, heteroaryl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to $C(=O)$, wherein each of said aryl, heteroaryl, cycloalkyl, cycloalkenyl, heterocycloalkyl, and heterocycloalkenyl is optionally substituted with 1-5 $R^{10}$;

$R^4$ is hydrogen, $C_{1-6}$ alkyl, $C_{2-6}$ alkenyl, $C_{2-6}$ alkynyl, or $C_{1-8}$ haloalkyl, wherein each of said alkyl, alkenyl, alkynyl, and haloalkyl is optionally substituted with one or more $R^9$; or $R^4$ is aryl, heteroaryl, cycloalkyl, cycloalkenyl, heterocycloalkyl or heterocycloalkenyl, wherein heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to $C(=O)$, wherein each of said aryl, heteroaryl, cycloalkyl, cycloalkenyl, heterocycloalkyl, and heterocycloalkenyl is optionally substituted with 1-5 $R^{10}$;

$R^5$ is hydrogen, $C_{1-6}$ alkyl, $C_{2-6}$ alkenyl, $C_{2-6}$ alkynyl, $C_{1-6}$ haloalkyl, $-C(=O)R^9$, $-S(=O)_{0-2}R^9$, $-S(=O)_{0-2}$-A-$R^9$ or -A-C(=O)$R^9$, wherein each of said alkyl, alkenyl, alkynyl, and haloalkyl is optionally substituted with one or more $R^9$; or $R^5$ is aryl, heteroaryl, cycloalkyl, cycloalkenyl, heterocycloalkyl or heterocycloalkenyl, wherein said heterocycloalkyl is optionally fused with a phenyl or a 5-6 membered heteroaryl, wherein one or more of the carbon atoms in said heterocycloalkyl or heterocycloalkenyl may be oxidized to $C(=O)$, wherein each of said aryl, heteroaryl, cycloalkyl, cycloalkenyl, heterocycloalkyl, and heterocycloalkenyl is optionally substituted with 1-5 $R^{10}$; or $R^4$ and $R^5$ taken together with the nitrogen to which they are attached form a heteroaryl, a heterocycloalkyl or a heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to $C(=O)$, wherein each of said heteroaryl, heterocycloalkyl, and heterocycloalkenyl is optionally substituted with 1-5 $R^{10}$;

each of $R^7$ and $R^8$ is independently hydrogen, $C_{1-8}$ alkyl, $C_{1-8}$ alkoxy, $C_{2-8}$ alkenyl, $C_{2-8}$ alkynyl, $C_{1-8}$ haloalkyl, or $C_{1-8}$ haloalkoxy; wherein each of said alkyl, alkenyl, alkynyl, haloalkyl, and haloalkoxy is optionally substituted with one or more $R^9$; or each of $R^7$ and $R^8$ is independently halogen, nitrile, nitro, hydroxyl, $-C(=O)R^9$, $-S(=O)_{0-2}R^9$, $-NR^4R^5$, $-O-A-R^9$, $-S(=O)_{0-2}$-A-$R^9$ or -A-C(=O)$R^9$; or each of $R^7$ and $R^8$ is independently aryl, heteroaryl, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to $C(=O)$, wherein each of said aryl, heteroaryl, cycloalkyl, cycloalkenyl, heterocycloalkyl, and heterocycloalkenyl is optionally substituted with 1-5 $R^{10}$; or $R^9$ is hydroxyl, $C_{1-6}$ alkoxy, $C_{1-8}$ haloalkoxy, $C_{3-6}$ cycloalkoxy or $-NR^{11}R^{12}$; or $R^9$ is aryl, heteroaryl, cycloalkyl, or cycloalkenyl, wherein each of said aryl, heteroaryl, cycloalkyl and cycloalkenyl are optionally substituted with 1-5 $R^{10}$; or $R^9$ is heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to $C(=O)$, wherein each of said heterocycloalkyl and said heterocycloalkenyl is optionally substituted with 1-5 $R^{10}$;

$R^{10}$ is nitro, nitrile, hydroxyl, halogen, $C_{1-6}$ acyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, cycloalkoxy, cycloalkyloxy, aryl, heteroaryl, $-NR^{11}R^{12}$, $-C(=O)OR^{11}$, $-C(=O)NHR^{11}$, $-NHC(=O)R^{13}$, $-NHS(=O)_2R^{13}$, $-S(=O)_{0-2}R^{13}$, $-S(=O)_2NHR^{11}$, cycloalkyl, cycloalkenyl, heterocycloalkyl or heterocycloalkenyl, wherein said heterocycloalkyl is optionally fused with a phenyl or a 5-6 membered heteroaryl having 1-3 heteroatoms, wherein one or more of the carbon atoms in said heterocycloalkyl or heterocycloalkenyl may be oxidized to $C(=O)$; wherein each of said alkyl, alkenyl, alkynyl, haloalkyl, alkoxy, haloalkoxy, cycloalkoxy, cycloalkyloxy, aryl, heteroaryl, cycloalkyl, cycloalkenyl, heterocycloalkyl, and heterocycloalkenyl is optionally substituted;

each of $R^{11}$ and $R^{12}$ is independently hydrogen, $C_{1-6}$ alkyl, $C_{2-6}$ alkenyl, $C_{2-6}$ alkynyl, $C_{1-6}$ haloalkyl, cycloalkyl or cycloalkenyl; wherein each of said alkyl, alkenyl, alkynyl, haloalkyl, cycloalkyl and cycloalkenyl is optionally substituted with one or more $R^9$;

$R^{13}$ is $C_{1-6}$ alkyl, $C_{2-6}$ alkenyl, $C_{2-6}$ alkynyl, $C_{1-6}$ haloalkyl, $C_{3-6}$ cycloalkyl or $C_{4-6}$ cycloalkenyl; wherein each of said alkyl, alkenyl, alkynyl, haloalkyl, cycloalkyl and cycloalkenyl is optionally substituted; and A is $C_{1-8}$ alkyl, $C_{2-8}$ alkenyl or $C_{1-8}$ haloalkyl.

20. A method according to claim 19, wherein $R^3$

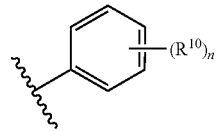

and n is 0-5, and pharmaceutically acceptable salts thereof.

* * * * *